(12) United States Patent
Striegel et al.

(10) Patent No.: US 6,867,211 B2
(45) Date of Patent: Mar. 15, 2005

(54) 4-PYRIDYL-AND 2,4-PYRIMIDINYL-SUBSTITUTED PYRROLE DERIVATIVES AND THEIR USE IN PHARMACY

(75) Inventors: Hans-Guenter Striegel, Blaustein (DE); Stefan Laufer, Blaubeuren (DE); Karola Tollmann, Blaubeuren (DE); Susanne Tries, Ehingen (DE)

(73) Assignee: Merckle GmbH, Blaubeuren (DE)

( * ) Notice: Subject to any disclaimer, the term of this patent is extended or adjusted under 35 U.S.C. 154(b) by 0 days.

(21) Appl. No.: 10/182,579

(22) PCT Filed: Jan. 31, 2001

(86) PCT No.: PCT/EP01/01011
§ 371 (c)(1),
(2), (4) Date: Nov. 5, 2002

(87) PCT Pub. No.: WO01/57042
PCT Pub. Date: Aug. 9, 2001

(65) Prior Publication Data
US 2003/0153558 A1 Aug. 14, 2003

(30) Foreign Application Priority Data
Feb. 1, 2000 (DE) .......................... 100 04 157

(51) Int. Cl.$^7$ .................... A61K 31/425; C07D 487/04; C07D 517/04; C07D 498/04; C07D 471/04
(52) U.S. Cl. ................ 514/256; 514/224.2; 514/230.5; 514/338; 544/48; 544/90; 544/333; 546/270.1; 546/271.7; 548/152; 548/217; 548/302.7
(58) Field of Search ............................ 514/224.2, 230.5, 514/256, 338; 554/48, 90, 333; 546/270.1, 271.7; 548/152, 217, 302.7

(56) References Cited

U.S. PATENT DOCUMENTS

| | | | |
|---|---|---|---|
| 3,920,672 A | 11/1975 | Untch et al. ............. | 260/306.7 |
| 4,536,512 A | 8/1985 | Biftu et al. .................. | 514/413 |
| 4,539,400 A | * 9/1985 | Fabre et al. .................... | 544/47 |
| 4,546,100 A | 10/1985 | Fabre et al. ................. | 514/231 |
| 4,560,699 A | 12/1985 | Muchowski et al. ........ | 514/413 |
| 4,584,297 A | 4/1986 | Fabre et al. ................. | 514/226 |
| 4,684,658 A | 8/1987 | Fabre et al. ................. | 514/338 |
| 4,719,218 A | 1/1988 | Bender et al. .............. | 514/300 |
| 4,873,340 A | * 10/1989 | Muchowski et al. ........ | 548/453 |
| 5,260,451 A | 11/1993 | Dannhardt et al. ......... | 548/453 |
| 5,459,152 A | * 10/1995 | Summers et al. ............ | 514/338 |
| 5,552,422 A | 9/1996 | Gauthier et al. ............ | 514/368 |
| 5,583,148 A | 12/1996 | Anderson et al. ........... | 514/339 |
| 5,631,122 A | 5/1997 | Mihayashi et al. .......... | 430/506 |
| 5,939,415 A | * 8/1999 | Laufer et al. ............... | 514/224.2 |
| 5,942,535 A | * 8/1999 | Laufer et al. ............... | 514/413 |
| 5,958,943 A | * 9/1999 | Laufer et al. ................ | 514/299 |

FOREIGN PATENT DOCUMENTS

| | | |
|---|---|---|
| DE | 198 45 446 A1 | 4/2000 |
| DE | 100 01 166 A1 | 7/2001 |
| EP | 0 043 858 A1 | 1/1982 |
| EP | 0 118 321 A1 | 9/1984 |
| EP | 0 147 317 A2 | 7/1985 |
| EP | 0 297 987 A1 | 1/1989 |
| EP | 0 525 823 B1 | 2/1993 |
| EP | 0 608 133 A1 | 7/1994 |
| WO | WO 95/32970 A1 | 12/1995 |
| WO | WO 95/32971 A1 | 12/1995 |
| WO | WO 95/32972 A1 | 12/1995 |
| WO | WO 01/00332 A1 | 1/2001 |
| WO | WO 01/05792 A1 | 1/2001 |
| WO | WO 01/06792 A1 | 1/2001 |

OTHER PUBLICATIONS

Dannhardt, G., et al., "Aminomethylierung und Arylthiolierung von 6.7–Diaryl–2.3–dihydro–1H–pyrrolizinen", *Arch. Pharm.*, vol. 319, pp. 65–69 (1986).

Dannhardt, G., et al., "Oxidative Ringöffnung von 6.7–Diphenyl–2.3–dihydro–1H–pyrrolizin (DADHP) durch m–Chlorperbenzoesäure", *Arch. Pharm.*, vol. 319, pp. 231–234 (1986).

Dannhardt, G., et al., "Synthese von 3–(6.7–Diphenyl–2.3–dihydro–1H–pyrrolizin–5–yl–propionsäure", *Arch. Pharm.*, vol. 319, pp. 234–237 (1986).

Dannhardt, G., et al., "Synthese und Oxidation von 6.7–Diphenyl–2.3–dihydro–1H–pyrrolizin–5–yl–acetaldehyd (DADHP–5–acetaldenhyd)", *Arch. Pharm.*, vol. 319, pp. 500–505 (1986).

Dannhardt, G., et al., "6.7–Diarylsubstituierte 1– und 3–Pyrrolizinone (1–DAPON und 3–DAPON)", *Arch. Pharm.*, vol. 319, pp. 749–755 (1986).

Dannhardt, G., et al., "Natriummetaperiodat–Oxidation von 6.7–Diphenyl–2.3–dihydro–1H–pyrrolizin", *Arch. Pharm.*, vol. 318, pp. 661–663 (1985).

Dannhardt, G., et al., "C–5 Functionalized 6,7–Diphenyl–2, 3–dihydro–1H–pyrrollizines as Inhibitors of Bovine Cyclooxygenase and 5–Lipoxygenase", *Arch. Pharm.*, vol. 327, pp. 509–514 (1994).

(List continued on next page.)

*Primary Examiner*—Richard L. Raymond
*Assistant Examiner*—Tamthom N. Truong
(74) *Attorney, Agent, or Firm*—Rothwell Figg Ernst & Manbeck

(57) ABSTRACT

The present invention relates to 4-pyridyl- and 2,4-pyrimidinyl-substituted pyrrole derivatives and their use in pharmacy, of the formula 1:

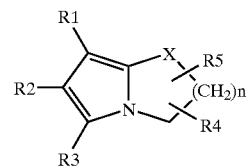

in which the variables have the meanings indicated in the description. The compounds according to the invention have immunomodulating and/or cytokine release-inhibiting action and are therefore utilizable for the treatment of disorders which are connected with a disturbance of the immune system.

3 Claims, No Drawings

OTHER PUBLICATIONS

Dannhardt, G., et al., "Dihydropyrrolizinyl–substituierte 2–Aminoethanol–und Glykolsäure–Derivate", *Chemiker–Zeitung*, vol. 110, pp. 124–128 (1986).

Dannhardt, G., et al., "Carbaldehyde und hydroxymethylierte Derivate Stellungsisomerer Diaryl–2, 3–dihydro–1H–pyrrolizines (5,6–,5,7–und 6,7–DADHP–Derivate", *Chemiker–Zeitung*, Vo. 110, pp. 267–271 (1986).

Dannhardt, G., et al., "Stellungsisomere Diaryldihydropyrrolizinyl–essigsäuren und–hydroxyethyl–Derivate", *Arch. Pharm.*, vol. 321, pp. 159–162 (1988).

Dannhardt, G., et al., "Stellungsisomere Diaryldihydropyrrolizinyl–ameisensäuren und–propionsäuren", *Arch. Pharm.*, vol. 321, pp. 545–549 (1988).

"Antiinflammatory Cyclooxygenase and 5–Lipooxygenase Inhibitor", Drugs of the Future, vol. 20, pp. 1007–1009 (1995), Rabasseda X. et al.

Laufer, S., et al., "Synthesis and Evaluation of a Novel Series of Pyrrolizine Derivatives as Dual Cyclooxygenase–1 and 5–Lipoxygenase Inhibitors", *Arch. Pharm.*, vol. 330, pp. 307–312 (1997).

Laufer, S., et al., "(6,7–Diaryldihydropyrrolizin–5–yl)acetic Acids, a Novel Class of Potent Dual Inhibitors of Both Cyclooxygenase and 5–Lipoxygenase", *J. Med. Chem.*, vol. 37, pp. 1894–1897 (1994).

Muchowski, J., et al. "Synthesis and Antiinflammatory and Analgesic Activity of 5–Aroyl–1,2–dihydro–3H–pyrrolo[1, 2–a] pyrrole–1–carboxylic Acids. The 6–Substituted Compounds", *J. Med. Chem.*, vol. 30, pp. 820–823 (1987).

* cited by examiner

4-PYRIDYL- AND 2,4-PYRIMIDINYL-SUBSTITUTED PYRROLE DERIVATIVES AND THEIR USE IN PHARMACY

The present invention relates to 4-pyridyl- and 2,4-pyrimidinyl-substituted pyrrole derivatives having immuno-modulating and cytokine release-inhibiting action, pharmaceutical compositions which contain these compounds, and their use in pharmacy.

Pharmacologically active pyrrolizine compounds which inhibit 5-lipoxygenase (5-LO) and cyclooxygenase-1 and -2 (Cox-1 and Cox-2) are already known.

For example, pyrrolizine compounds having anti-inflammatory activity are described in Arch. Pharm. 319, 231–234 (1986), 318, 661–663 (1985), 318, 663–664 (1985), 319, 500–505 (1986), 319, 749–755 (1986), 327, 509–514 (1994), 330, 307–312 (1997), and in J. Med. Chem. 1987, 30, 820–823 and 1994, 37, 1894–1897. The most promising compound of this type is the 6-(4-chloro-phenyl)-7-phenyl-2,3-dihydropyrrolo[1,2-a]pyrrole compound ML 3000, see Drugs of the Future, 1995, 20, (10).: 1007–1009. It suppresses the release of leukotrienes, thromboxanes and prostaglandins. The inhibitory action on the formation of the leukotrienes and the prostaglandins is balanced in this structure, harmful effects of a pure inhibitory action on cyclooxygenase -1 and -2 (Cox-1 or Cox-2) with increased formation of leukotrienes are not observed here. In all these compounds, the 1-position of the pyrrolizine structure is unsubstituted.

WO 95/32970, WO 95/32971 and WO 95/32972 relate to compounds of the formula:

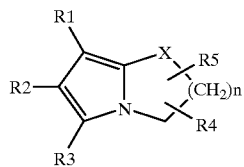

where one or two of the radicals $R^1$, $R^2$ and $R^3$ can be a mono- or bicyclic, aromatic, heterocyclic radical which has at least one oxygen, sulfur and/or nitrogen atom. These compounds have anti-inflammatory action.

Further fused pyrrole compounds and structurally similar compounds pounds are described in U.S. Pat. Nos. 5,260,451, 4,546,100 and 4,584,297; 4,684,658; 5,631,122; 3,920,672; 4,536,512; 5,552,422; 4,539,400; 4,719,218; EP 608 133 A, DE 198 45 446 A, PCT/EP 99/09057 and DE 100 01 166. It is not disclosed that these compounds have immunomodulating or cytokine release-inhibiting action.

Surprisingly, it has now been found that certain fused pyrrole compounds which have a 4-pyridyl substituent on the pyrrole ring have immunomodulating and/or cytokine release-inhibiting action.

The present invention therefore relates to the 4-pyridyl- and 2,4-pyrimidinyl-substituted pyrrole derivatives and their use in pharmacy, of the formula I:

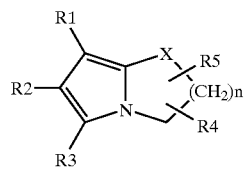

in which
one of the radicals $R^1$, $R^2$ and $R^3$ is a group of the formula:

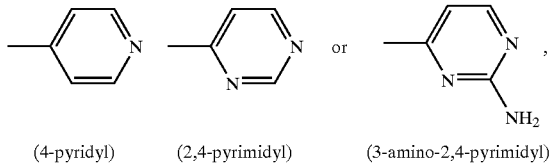

(4-pyridyl)   (2,4-pyrimidyl)   (3-amino-2,4-pyrimidyl)

which is optionally substituted by one or two $C_1$–$C_4$-alkyl groups or halogen atoms,
the second of the radicals $R^1$, $R^2$ and $R^3$ is phenyl or thienyl, which is optionally substituted by one or two halogen atoms, and
the third of the radicals $R^1$, $R^2$ and $R^3$ is H, $CO_2H$, $CO_2C_1$–$C_6$-alkyl, $CH_2OH$ or $C_1$–$C_6$-alkyl,
$R^4$ and $R^5$ independently of one another are H or $C_1$–$C_6$-alkyl,
X is $CH_2$, S or O and
n is 1 or 2,
and the optical isomers, physiologically tolerable salts and physiologically easily hydrolyzable esters thereof.

In the present case, the physiologically tolerable salts can be acid addition salts or base addition salts. For acid addition salts inorganic acids are used, such as hydrochloric acid, sulfuric acid or phosphoric acid, or organic acids, such as tartaric acid, citric acid, maleic acid, fumaric acid, malic acid, mandelic acid, ascorbic acid, gluconic acid and the like.

Base addition salts include salts of the compounds of the formula I with inorganic bases, such as sodium or potassium hydroxide, or with organic bases, such as mono-, di- or triethanolamine.

Physiologically easily hydrolyzable esters of the compounds of the formula I are, for example, alkyl, pivaloyloxymethyl, acetoxymethyl, phthalidyl, indanyl and methoxymethyl esters.

If the compounds according to the invention have asymmetric centers, racemates and optical isomers (enantiomers, diastereomers) are included.

The expression "$C_1$–$C_6$-alkyl" includes straight-chain or branched alkyl groups, such as methyl, ethyl, n-propyl, i-propyl, n-, i- or t-butyl, sec-butyl, n-pentyl and n-hexyl.

The expression "halogen" includes a fluorine, chlorine, bromine or iodine atom and in particular a fluorine or chlorine atom.

If the second of the radicals $R^1$, $R^2$ and $R^3$ is phenyl, this is preferably substituted by a halogen atom, in particular a fluorine atom. Preferably, the halogen atom is situated in the 4-position.

If the second of the radicals $R^1$, $R^2$ and $R^3$ is thienyl, this is preferably bonded in the 2-position. If the 2-thienyl group is substituted, it is preferably substituted with a halogen atom and in particular in the 5-position.

The preparation of the compounds according to the invention is carried out according to various processes, depending on the position of the aromatic radicals and depending on the nature of the heteroaromatic radicals $R^1$, $R^2$ and $R^3$.

The [α]-heterocyclically fused pyrrole compounds, in which X=S, or O, are prepared analogously to the processes described in WO 95/32970, WO 95/32971 and WO 95/32972.

Examples 23 and 24 describe how 5H-furan-2-one precursors are condensed with the acetic acid salts of aminoalcohols to give 1-hydroxyalkyl-2-pyrrolones, which afford the [α]-hetero-cyclically fused pyrrole compounds with suitable condensing agents (here $P_2S_5$ or methanesulfonyl chloride) (scheme 1).

In the group consisting of the pyrrolizines, N-acyl derivatives of proline (pyrrolidine-2-carboxylic acid, cf. examples 1–9, 19, 20, 22) are employed for sydnone formation, in the group consisting of the thiazolo [2,1-b]pyrroles (cf. examples 10–14) the N-acyl derivatives of [1,3]-thiazolidine-2-carboxylic acid) are used and in the group consisting of the indolizines N-acyl derivatives of the homologous piperidine-2-carboxylic acid (cf. examples 15–18) are used.

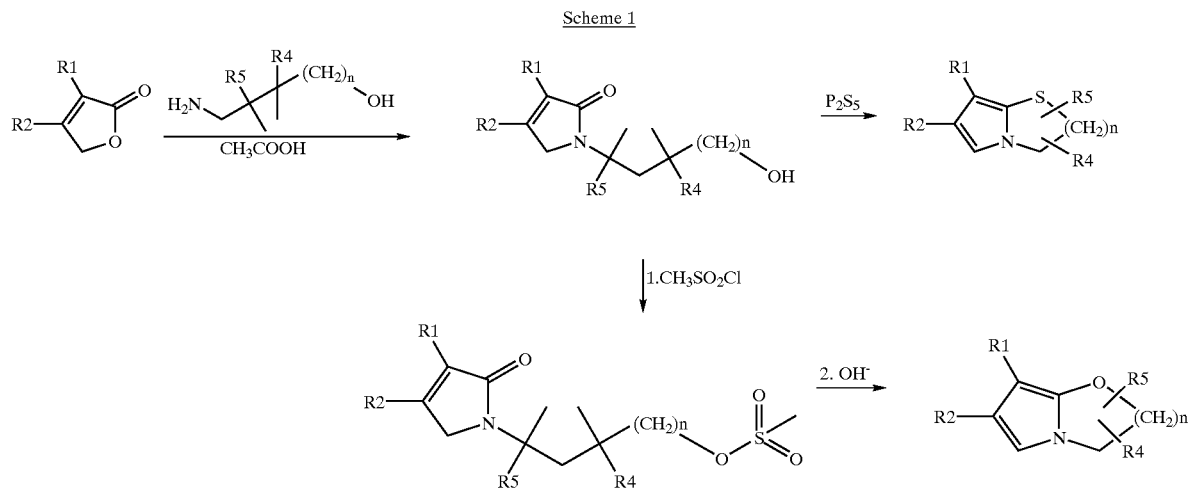

Scheme 1

The synthesis of the pyrrolizines, indolizines and their 1-thia analogs, with preferred positioning of pyridine and pyrimidine radical in position 5 or 6 ($R^3$) and 6 or 7 ($R^2$), is carried out in the manner of a 1,3-dipolar cycloaddition from appropriate münchnone or sydnone precursor compounds and suitable dienophiles or dipolarophiles (scheme 2).

For example, the cycloaddition of ethyl 2-bromo-3-(4-pyridyl)-propenoate to the in situ-generated münchnone of N-(4-fluoro-benzoyl)proline to give the ester from example 1, of ethyl 2-bromo-3-(4-fluorophenyl)propenoate to the münchnone of N-(isonicotinoyl)proline to give the ethyl ester

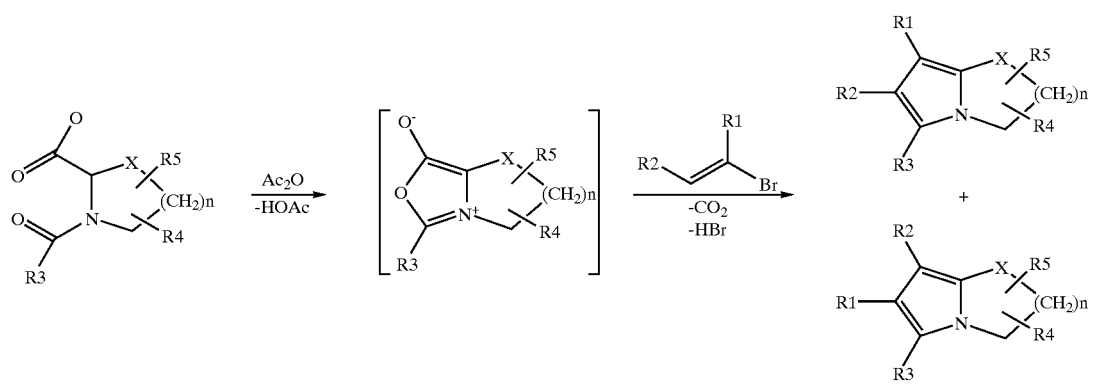

Scheme 2

In this case, a pyridine or pyrimidine radical can be introduced on the one hand via the münchnone/sydnone component, on the other hand via the dipolarophile component. The dipolarophiles used are dehydrocinnamic acid esters, 3-substituted acetylenecarboxylic acid esters, 2-halogen-substituted cinnamic acids or 2-haloacrylates and nitrostyrenes.

of the pyrrolizinecarboxylic acid of example 19 and the cycloaddition of an ethyl 2-bromo-3-(4-fluorophenyl) propenoate to the intramolecularly cyclized 3-(4-fluorobenzoyl)-[1,3]-thiazol-idine-2-carboxylic acid leads to the pyrrolizine compound from example 10.

By the use of 1-nitrostyrenes and N-aroylproline, 7-(or 1-) unsubstituted 5,6- (or 2,3-)diarylpyrrolizine compounds are obtained directly.

The reaction of 1-fluoro-4-(2-nitrovinyl)benzene with 1-pyridine-4-carbonylpyrrolidine-2-carboxylic acid (N-isonicotinoyl-proline) leads to the compound from example 22.

Pyridine and pyrimidine substituents can also be introduced subsequently into the activated pyrrole positions of the pyrrolizines and indolizines and their thia and oxa analogs (schemes 3 and 4). The reaction of 6-(4-fluorophenyl)-7-methyl-2,3-dihydro-1H-pyrrolizine with the reactive 1-ethoxycarbonyl-pyridinium chloride obtained from ethyl chloroformate and pyridine affords the compound of example 21 ($R^1$=$CH_3$, $R^2$=4-fluorophenyl).

Scheme 3

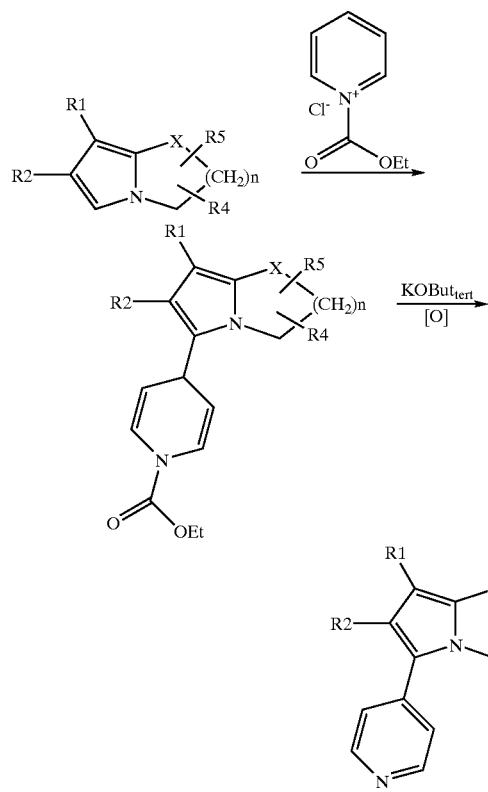

Scheme 4

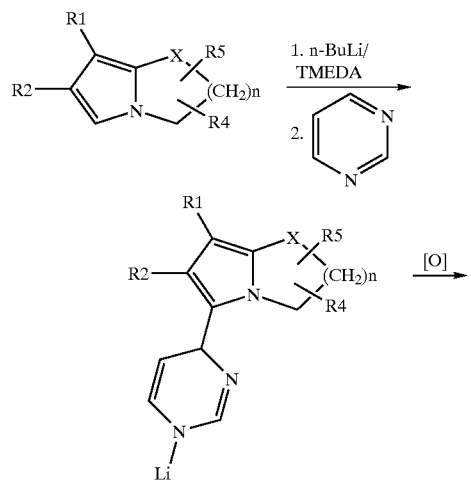

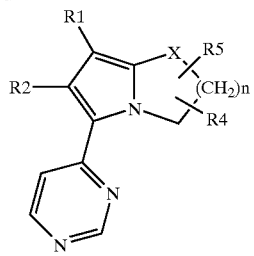

In particular the 3-amino-2,4-pyrimidine substituent can be synthesized starting from the acyl derivatives of the monoaryl-substituted compounds via condensation with dimethylformamide dimethyl acetal and guanidine (scheme 5).

The 3-amino-2,4-pyrimidine substituent can be introduced according to this method into each reactive, unsubstituted position of the pyrrole ring of the pyrrolizidine and indolizidine system.

Scheme 5

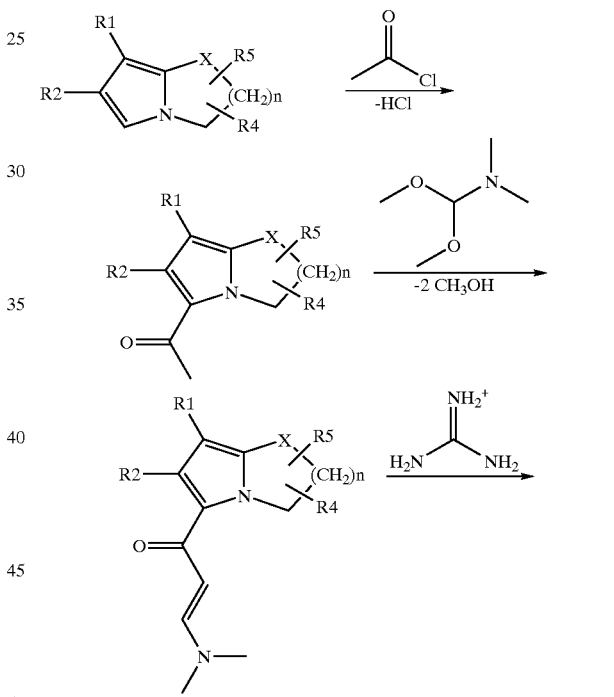

The compounds according to the invention show in vitro and in vivo immunomodulating and cytokine release-inhibiting action. They are thus suitable for the treatment of disorders which are connected with a disturbance of the immune system. For example, they are utilizable for the treatment of autoimmune diseases, cancer, multiple sclerosis, arthritis, inflammatory bowel disease, septic shock, adult respiratory distress syndrome, and in transplantations.

The compounds according to the invention can be administered either as individual therapeutic active compounds or as mixtures with other therapeutic active compounds. They can be administered as such, but in general they are administered in the form of pharmaceutical compositions, i.e. as mixtures of the active compounds with suitable pharmaceutical carriers or diluents. The compounds or compositions can be administered orally or parenterally, but preferably they are given in oral dosage forms.

The type of pharmaceutical composition and of pharmaceutical carrier or diluent depends on the desired type of administration. Oral compositions can be present, for example, as tablets or capsules and can contain customary excipients, such as binders (e.g. syrup, acacia, gelatin, sorbitol, tragacanth or polyvinylpyrrolidone), fillers (e.g. lactose, sugar, cornstarch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations can be present in the form of aqueous or oily suspensions, solutions, emulsions, syrups, elixirs or sprays etc. or as dry powders for reconstitution with water or another suitable carrier. Liquid preparations of this type can contain customary additives, for example suspending agents, flavorings, diluents or emulsifiers. For parenteral administration, solutions or suspensions with customary pharmaceutical carriers can be employed.

The compounds or compositions according to the invention can be administered to a mammal (human or animal) in doses of approximately 0.5 mg to approximately 100 mg per kg of body weight per day. They can be administered in an individual dose or in a number of doses. The spectrum of action of the compounds was investigated with the aid of the following test systems.

In vitro Test Procedure Using Human Whole Blood

Human potassium-EDTA whole blood (at 400 $\mu$l) is preincubated with test substance for 15 min. at 37° C. in a $CO_2$ incubator (5% $CO_2$; 95% moisture-saturated air). The samples are then stimulated for 4 hours with 1 $\mu$g/ml of LPS (*E. coli* 026:B6) at 37° C. in a $CO_2$ incubator (5% $CO_2$; 95% moisture-saturated air). The reaction is ended by placing the samples on ice, addition of DPBS buffer and subsequent centrifugation (1000×g; 15 min). The plasma supernatant is used for the quantification of IL-1$\beta$ and TNF$\alpha$ by means of ELISA.

In vitro Test Procedure Using PBMCs

The mononuclear cells (PBMCs) are isolated from human potassium-EDTA whole blood diluted 1:3 by means of density gradient centrifugation (Histopaque®-1.077). After 2 washing steps with DPBS buffer, the mononuclear cells are resuspended in macrophage-SFM medium and adjusted to a cell count of 1×10$^6$ cells/ml.

The PBMCs suspension (at 390 $\mu$l) is preincubated with test substance for 15 min at 37° C. in a $CO_2$ incubator (5% $CO_2$; 95% moisture-saturated air). The samples are subsequently stimulated for 4 hours with 1 $\mu$g/ml LPS (*E.coli* 026:B6) at 37° C. in a $CO_2$ incubator (5% $CO_2$, 95% moisture-saturated air). The reaction is ended by placing the samples on ice, addition of DPBS buffer and centrifugation (15880×g; 12 min). The supernatant is used for the quantification of IL-1$\beta$ and TNF$\alpha$ by means of ELISA.

In vitro Test System for Determining the Inhibition of 5-lipoxygenase

Human granulocytes are used as a source of the 5-lipoxygenase. LTB4 (leukotriene B4) is formed from endogenous arachidonic acid by means of stimulation with calcium ionophore A 23187. The granulocytes are isolated and the enzyme reaction is carried out according to known processes (see Arch. Pharm. Pharm. Med. Chem. 330, 307–312 (1997)).

The blood, which is protected from clotting with heparin, is centrifuged on a discontinuous Percoll® gradient and the granulocyte layer is pipetted off. After lysis of the erythrocytes, the granulocytes are washed a number of times and then adjusted to a specific cell count. The enzyme reaction is then started with calcium ionophore A 23187 in the presence or absence of the test substance after addition of Ca2+. The synthesis of the leukotrienes is stopped after 1.5 minutes. The samples are centrifuged off and the supernatant is diluted. LTB4 is determined quantitatively by means of ELISA.

In vitro Test System for Determining the Inhibition of Cyclooxygenase-1

In this test system, the amount of prostaglandin E2 formed from human platelets after addition of calcium ionophore is determined by means of ELISA. In this process, the platelets are obtained after centrifugation on a discontinuous Percoll® gradient. The enzyme reaction and the determination of the metabolites formed is carried out in principle as in the determination of 5-lipoxygenase inhibition. Differences exist with respect to the incubation time. Furthermore, the addition of a thromboxane synthesis inhibitor is necessary (see Arch. Pharm. Pharm. Med. Chem. 330, 307–312 (1997)).

In vitro Test System for Determining the Inhibition of Cyclooxygenase-2

COX2 (from sheep placenta) is preincubated at 4° C. with test substance for 10 min, then stimulated with arachidonic acid (5 $\mu$M) at 25° C. for 10 min. Diclofenac is used as a reference (IC50(COX2)=3.0 10$^{-6}$ M). The determination is carried out at 3 dilutions (10$^{-7}$, 10$^{-6}$, 10$^{-5}$ M). The PGE2 concentrations are quantified by means of ELISA (see Mitchell J. A. et al., Proc. Nat. Acad. Sci. 90: 11693–11697 (1993)).

TABLE 1

Influence of the test compounds on the release of inflammatory mediators (IC$_{50}$ values in μmol, and percentage inhibition in μmol [μmol/%]):

| Example | Structure | COX-1 | COX-2 | 5-LO | TNFα | IL-1β |
|---|---|---|---|---|---|---|
| 1A | [structure: pyrrolizine with COOEt, pyridin-4-yl, and 4-fluorophenyl substituents] | — | — | — | PBMC: 10/13 whole-blood method: 30 | PBMC: 10/21 whole-blood method: 30 |
| 2 | [structure: pyrrolizine with COOH, pyridin-4-yl, and 4-fluorophenyl substituents] | — | — | — | PBMC: 10/37 whole-blood method: 16 | PBMC: 10/17 whole-blood method: 2.9 |
| 3 | [structure: pyrrolizine with CH$_2$OH, pyridin-4-yl, and 4-fluorophenyl substituents] | — | 5.7 | 3.7 | PBMC: 4.0 whole-blood method: 28 | PBMC: 5.0 whole-blood method: 22 |
| 4 | [structure: pyrrolizine with CH$_3$, pyridin-4-yl, and 4-fluorophenyl substituents] | 1.9 | 3.4 | 2.4 | PBMC: 6.0 whole-blood method: 41 | PBMC: 5.7 whole-blood method: 59 |
| 5 | [structure: pyrrolizine with pyridin-4-yl, and 4-fluorophenyl substituents] | — | 5.8 | 0.027 | PBMC: 1.4 10/88 1/44 | PBMC: 10/— |

TABLE 1-continued

Influence of the test compounds on the release of inflammatory mediators (IC$_{50}$ values in μmol, and percentage inhibition in μmol [μmol/%]):

| Example | Structure | COX-1 | COX-2 | 5-LO | TNFα | IL-1β |
|---------|-----------|-------|-------|------|------|-------|
| 1B | [structure: pyrrolizine with pyridine, COOEt, and 4-fluorophenyl substituents] | — | n.d. | 2.0 | PBMC: 1.4 10/60 1/12 | PBMC: 1.4 10/− 1/+ |
| 7 | [structure: pyrrolizine with COOH, pyridine, and thiophene substituents] | 10/40 | | | whole-blood method: 48 | whole-blood method: 52 |
| 9A | [structure: pyrrolizine with COOEt, pyridine, and 5-chlorothiophene substituents] | 10/11 | | 1.3 | PBMC: 10/38 whole-blood method: 38 | PBMC: 10/47 whole-blood method: 22 |
| 10A | [structure: thiazolo-pyrrole with COOEt, pyridine, and 4-fluorophenyl substituents] | 3.4 | 6.1 | 0.065 | PBMC: 10.0 whole-blood method: 30 | PBMC: >100.0 whole-blood method: 30 |
| 11 | [structure: thiazolo-pyrrole with COOH, pyridine, and 4-fluorophenyl substituents] | 10/33 | — | 10/30 | PBMC: 6.8 whole-blood method: 100/45 | PBMC: 2.3 whole-blood method: 100/45 |

TABLE 1-continued

Influence of the test compounds on the release of inflammatory mediators (IC$_{50}$ values in μmol, and percentage inhibition in μmol [μmol/%]):

| Example | Structure | COX-1 | COX-2 | 5-LO | TNFα | IL-1β |
|---|---|---|---|---|---|---|
| 12 | 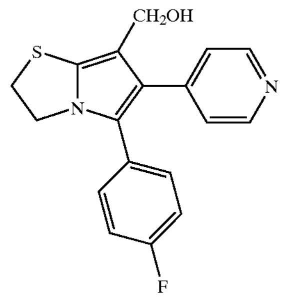 | | | | PBMC: 10/44 whole-blood method: 45 | PBMC: 7.6 whole-blood method: 76 |
| 13 | 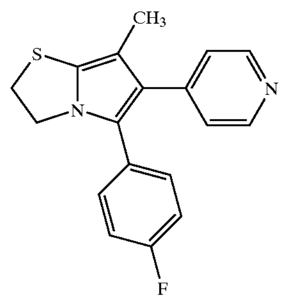 | 10/45 | | 0.04 | PBMC: 8.1 whole-blood method: 41 | PBMC: 10/43 whole-blood method: 80 |
| 14 | 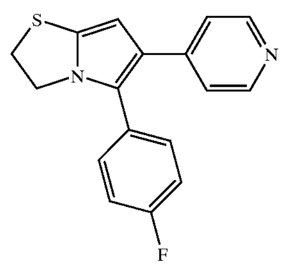 | 2.3 | | 2.4 | PBMC: 7.6 whole-blood method: — | PBMC: 8.5 |
| 17 | 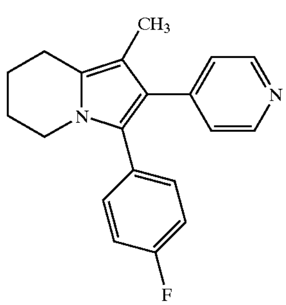 | 10/48 | | 2.2 | PBMC: 4.0 whole-blood method: 39 | PBMC: 10.0/67 1.0/0.0 whole-blood method: 33 |
| 18 | 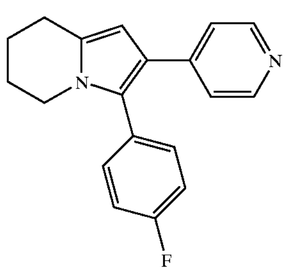 | 10/35 | 1.6 | 3.3 | PBMC: 10.0/65 1.0/33 0.1/16 whole-blood method: 37 | PBMC: 7.5 whole-blood method: 36 |

TABLE 1-continued

Influence of the test compounds on the release of inflammatory mediators ($IC_{50}$ values in μmol, and percentage inhibition in μmol [μmol/%]):

| Example | Structure | COX-1 | COX-2 | 5-LO | TNFα | IL-1β |
|---|---|---|---|---|---|---|
| 19A | 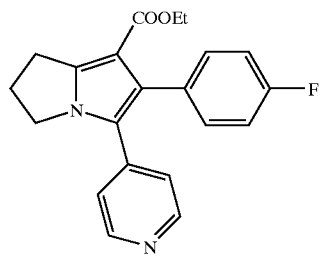 | 2.9 | 5.5 | 2.05 | PBMC:<br>10.0/60<br>1.0/0 | PBMC:<br>10.0/21<br>1.0/0 |
| 21 | 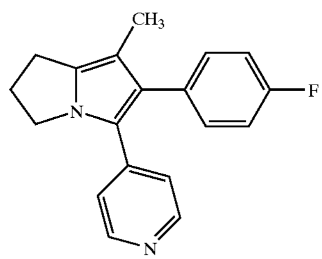 | 0.13 | PBMC:<br>0.34<br>whole-blood<br>method:<br>6.0<br>10/33 | — | PBMC:<br>26 | PBMC:<br>5.6<br>whole-blood<br>method:<br>37 |
| 22 | 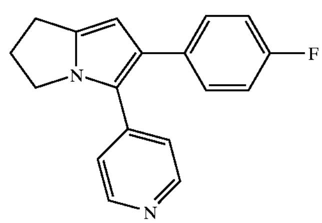 | 0.23 | 1.5 | 0.67 | PBMC:<br>10/34 | PBMC:<br>10/59<br>1/+ |
| 23 | 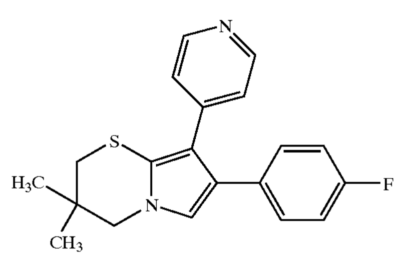 | 10/83<br>1.0/0<br>3.5 | PBMC:<br>10/50<br>1/10<br>4.0 | 0.05 | PBMC:<br>10/79<br>1/0 | PBMC:<br>1/19 |
| 24 | 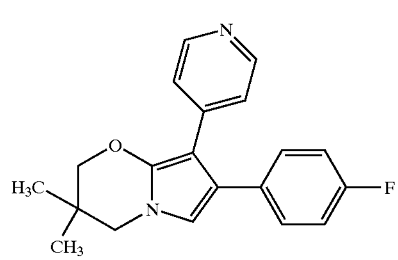 | | 4.0 | 1.35 | PBMC:<br>10/42 | PBMC:<br>10/48 |

TABLE 1-continued

Influence of the test compounds on the release of inflammatory mediators ($IC_{50}$ values in µmol, and percentage inhibition in µmol [µmol/%]):

| Example | Structure | COX-1 | COX-2 | 5-LO | TNFα | IL-1β |
|---|---|---|---|---|---|---|
| 25 | 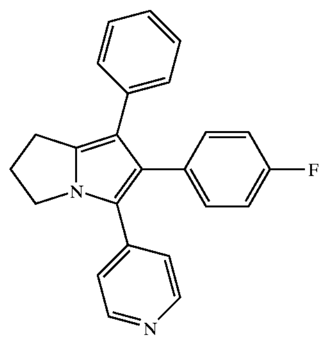 | — | — | — | PBMC: 87 | PBMC: 100/+++ |

PBMC: peripheral blood mononuclear cells

EXAMPLE 1A
Ethyl 3-(4-fluorophenyl)-2-(4-pyridyl)-6,7-dihydro-5H-pyrrolizine-1-carboxylate a) N-(4-Fluorobenzoyl)proline L-Proline (15.0 g, 130 mmol) is dissolved in NaOH (5%, 150 ml, 190 mmol) and the solution is cooled in an ice bath (0–5° C.). 4-Fluorobenzoyl chloride (19.0 g, 120 mmol) is added dropwise with vigorous stirring, the cooling is removed and stirring is continued for 1 h. After acidifying the reaction mixture with HCl (10% strength, 45 ml) the amide deposits in large lumps, which are comminuted, suspended using water, filtered off with suction and washed with water (50 ml). The substance is dried over $P_2O_5$ in vacuo: 24.41 g.

M.p.: 174.0° C., yield: 79%; $C_{12}H_{12}FNO_3$; MW=237.23.

IR (KBr): 1/λ ($cm^{-1}$)=1735, 1605, 1585, 1514, 1440, 1230, 1180, 1161, 856, 762 513;

$^1$H-NMR ($CDCl_3$:) δ[ppm]=7.64–7.57 (m, 2H,); 7.16–7.07 (m, 2H); 4.78–4.71 (m, CH); 3.63–3.57($CH_2$); 2.36–1.85 (m; 2 $CH_2$).

b) Bromocarbethoxymethylenetriphenylphosphorane

Carboethoxymethyltriphenylphosphonium bromide (43 g, 100 mmol) is dissolved in water (100 ml) and cooled in an ice bath. NaOH (10%, 40 ml, 100 mmol) is added dropwise at 0–5° C. until a pH of 9 is reached. The deposited resinous mass is separated off, digested with ether and the crystals formed are filtered off with suction (31 g, 87%). The substance is dried over $CaCl_2$ in a desiccator in the dark.

The dried compound (carboethoxymethylidenetriphenylphosphorane, 30 g, 0.086 mol) is dissolved in $CH_2Cl_2$ (160 ml) and the solution is cooled to 5° C. in an ice bath. A solution of bromine (13.9 g, 0.087 mol) in $CH_2Cl_2$ (40 ml) is slowly added dropwise and the batch is stirred for a further 30 min until the disappearance of the bromine coloration.

The organic phase is washed first with water (50 ml), then twice with $NaHCO_3$ solution (100 ml) in a separating funnel until all of the HBr is neutralized. The $CH_2Cl_2$ phase is dried over $Na_2SO_4$ sicc. and concentrated in vacuo. The residue is crystallized from acetone/n-hexane (60 ml, 2:1). The crystals are washed with this mixture (40 ml) and dried in vacuo: 27.5 g.

M.p.: 151.9° C., yield: 75%; $C_{22}H_{20}BrO_2P$; MW=427.28.

IR (KBr): 1/λ ($cm^{-1}$)=2981, 1650, 1583, 1434, 1301, 1101, 693;

$^1$H-NMR ($CDCl_3$:) δ[ppm]=7.73–7.44 (m; 15H, ar.); 3.935 (q; J=7 Hz, 2H); 0.885 (t; J=7 Hz, $CH_3$).

$^{13}$C-NMR ($CDCl_3$:) δ[ppm]=162.5, 149.8, 141.8, 137.9, 123.7, 118.1, 63.2, 14.1.

c) Ethyl 2-bromo-3-(4-pyridyl)propenoate

Bromocarbethoxymethylenetriphenylphosporane (9.0 g, 21 mmol) is dissolved in toluene (60 ml) with the exclusion of light and then a solution of isonicotinaldehyde (4-pyridinecarbaldehyde, 2.14 g, 20 mmol) in toluene (9 ml) is added. The batch is stirred in the dark at RT for 16 h. The solution is then concentrated in vacuo, the residue is digested with ether (40 ml) and the ether phase is filtered off with suction from the crystalline solid. The crystals are washed a further 2 times with ether (10 ml) and the collected ether solutions are concentrated in vacuo. The residue which remains (6.63 g) is purified by column chromatography (cc) on $Al_2O_3$ using an ether/n-hexane mixture (2:1). The substance sought appears in the fractions 1–5: 4.9 g of dark brown oil.

Yield: 95.7%; $C_{10}H_{10}BrNO_2$; MW=256.10.;

$^1$H-NMR ($CDCl_3$:) δ[ppm]: 8.72–8.69/7.66–7.63 (AA'BB'; 4H, ar.); 8.12 (s, 1H); 4.43–4.32 (q, J=7.1 Hz, 2H, $CH_2$); 1.44–1.37 (t; J=7.1 Hz, $CH_3$)

$^{13}$C-NMR ($CDCl_3$:) δ[ppm]: 162.5,; 149.8,; 141.8,; 137.9,; 123.7,; 118.1,; 63.2,; 14.1 d) Ethyl 3-(4-fluorophenyl)-2-(4-pyridyl)-6,7-dihydro-5H-pyrrolizine-1-carboxylate N-(4-Fluorobenzoyl)proline (9.48 g, 40 mmol) is suspended in acetic anhydride (60 ml), raised to a temperature of 80° C. in a reflux apparatus under argon until a clear solution is obtained (20 min), then treated dropwise with ethyl 2-bromo-3-(4-pyridyl)acrylate (12.28 g, 8 mmol) in toluene (10 ml) (8 min) and the reaction vessel is immersed in a prepared hot oil bath (120° C.). The dark mixture is heated under reflux for 21 h, whereupon starting material is no longer detectable by tlc ($Al_2O_3$; ethyl acetate/n-hexane 1:1). The reaction solution is cooled and treated with ethyl acetate (50 ml), and the organic supernatant is poured off. The solid deposited in the flask is digested 2 times with ethyl acetate (30 ml) in the presence of heat. Supernatant and ethyl acetate solutions are combined and concentrated in vacuo. The residue is taken up in ethyl acetate (200 ml) and the ethyl acetate phase is washed until neutral with water (100 ml), $NaHCO_3$ solution (100 ml) and water again (100 ml), dried ($Na_2SO_4$ sicc.) and concentrated. A pale beige solid crystallizes from the concentrated ethyl acetate phase (30 ml). After filtering off with suction, washing (ethyl acetate) and after drying, 2.93 g of the product sought remain.

After concentrating the mother liquor, a further 2.1 g of a crystallizate are obtained which is a mixture of product and by-product.

Yield: 21%, $C_{21}H_{19}FN_2O_2$; MW=350.40.

IR (KBr): $1/\lambda$ (cm$^{-1}$)=2985, 1695, 1510, 1222, 1136, 1093, 839, 584, 525

$^1$H-NMR (CDCl$_3$:) δ[ppm]=8.46–8.43/7.14–7.11 (AA'BB'; 4H, -pyridyl); 7.10–6.92 (m; 4H, ar.); 4.22–4.12 (q; J=7.1 Hz, 2H); 4.02–3.95 (t; J=7.2 Hz, 2H); 3.27–3.19 (t; J=7.5 Hz, 2H); 2.63–2.48 (m; J=7.3 Hz, 2H); 1.24–1.17 (t; J=7.2 Hz, CH$_3$)

$^{13}$C-NMR (d$_6$-DMSO): δ[ppm]=164.5, 148.9, 145.2, 143.5, 131.1, 131.0, 127.2, 156.0, 115.8, 115.4, 59.4, 46.8, 26.6, 26.4, 14.3.

EXAMPLE 1B

Ethyl 3-(4-fluorophenyl)-1-(4-pyridyl)-6,7-dihydro-5H-pyrrolizine-2-carboxylate

CC separation of the mixed crystallizate (2.1 g) obtained under example 1A, d):

Separation on Al$_2$O$_3$— ether/THF 9:1: fractions 6–9: substance 1A (1.15 g)

Fraction 10–12: mixture of 1A+1B;

fractions 13–end: substance 1B (0.3 g);

yield: 0.3 g (2%) $C_{21}H_{19}FN_2O_2$; MW=350.40.

IR (KBr): $1/\lambda$ (cm$^{-1}$)=2983, 1702, 1600, 1523, 1489, 1435, 1218, 1171, 1161, 1028, 849, 834, $^1$H-NMR (CDCl$_3$) δ[ppm]=8.56–8.53/7.32–7.29 (m; 4H, pyridyl); 7.48–7.41/7.16–7.07 (m; 4H, ar.); 4.09–3.99 (q; J=7.1 Hz, 2H); 3.92–3.85 (t; 7.1 Hz, CH$_2$); 3.03–2.95 (t; J=7.3 Hz, CH$_2$); 2.58–2.48 (quin; J=5.4 Hz, CH$_2$); 1.02–0.94 (t; J=7.2 Hz, CH$_3$)

$^{13}$C-NMR (CDCl$_3$): δ[ppm]=165.1; 163.8; 160.1; 149.2; 143.7; 136.7; 133.0; 131.8; 131.6; 127.8; 123.8; 115.2; 114.8; 59.7; 46.1; 27.0; 24.5; 13.7

EXAMPLE 2

3-(4-Fluorophenyl)-2-(4-pyridyl)-6,7-dihydro-5H-pyrrolizine-1-carboxylic acid

Ethyl 3-(4-fluorophenyl)-2-(4-pyridyl)-6,7-dihydro-5H-pyrrolizine-1-carboxylate (example 1A, 1.0 g, 2.8 mmol) is refluxed in an ethanolic KOH (10%, 10 ml, 18 mmol) for 16 h. The ethanol is then evaporated in vacuo, and the residue is taken up in water (10 ml) and neutralized using dil. HCl until the free acid has completely deposited. This is filtered off with suction, washed with water and dried in vacuo. 0.78 g is obtained.

M.p.: dec.; yield: 85%; $C_{19}H_{15}FN_2O_2$; MW=322.34.

IR (KBr): $1/\lambda$ (cm$^{-1}$)=1683, 1602, 1512, 1149;

$^1$H-NMR (CDCl$_3$/d$_6$-DMSO) δ[ppm]=8.40–8.37/ 7.19–7.16 (AA'BB'; 4H, -pyridyl); 7.07–6.92 (m; 4H, ar.); 3.98 (t; J=7.1 Hz, CH$_2$); 3.23 (t; J=7.4 Hz, CH$_2$) 2.92 (s; OH); 2.54 (t; J=7.3 Hz, CH$_3$)

$^{13}$C-NMR (CDCl$_3$/d$_6$-DMSO): δ[ppm]=165.8, 164.2, 159.3,; 148.4,; 145.3,; 143.6, 131.2, 131.0, 127.4, 127.3, 126.5, 126.0, 123.8, 115.6, 115.2, 105.9, 46.6, 26.5, 26.2.

EXAMPLE 3

[3-(4-Fluorophenyl)-2-(4-pyridyl)-6,7-dihydro-5H-pyrrolizin-1-yl]methanol

Ethyl 3-(4-fluorophenyl)-2-(4-pyridyl)-6,7-dihydro-5H-pyrrolizine-1-carboxylate (example 1A, 4.56 g, 13 mmol) is dissolved in abs. THF (100 ml) under argon and Na bis-methoxyethoxyaluminum hydride (Vitride$^R$) is added drop-wise through a septum via the cannula of a syringe (20 min). The mixture is stirred at 50° C. for 2 h, whereupon starting material is no longer detectable by tlc (Al$_2$O$_3$—ethyl acetate/n-hexane 3:7), then it is allowed to cool. H$_2$O (25 ml) is cautiously added dropwise to the reaction solution, then it is concentrated in vacuo (THF evaporates), and the aqueous organic residue is treated with ethyl acetate (100 ml). The phases are separated. The organic phase is washed 2 times with water (40 ml), dried over Na$_2$SO$_4$ sicc. and concentrated in vacuo (5.0 g). The reddish brown-colored, resinous residue is crystallized from diethyl ether (10 ml). The crystals are washed with ethyl acetate (5 ml) and ether (5 ml) and dried. 3.67 g of the compound sought remain Yield: 91.5%; $C_{19}H_{17}FN_2O$; MW=308.35;

$^1$H-NMR (CDCl$_3$): δ[ppm]=8.43–8.40 and 7.21–7.18 (AA'BB'; 4H, -pyridyl); 7.18–7.12 (m; 2H, ar.); 7.05–6.95 (m; 2H, ar.); 4.55 (s; CH$_2$); 3.96 (t; J=7.0 Hz, CH$_2$); 3.01 (t; J=7.3 Hz, CH$_2$); 2.53 (quin; J=7.1 Hz, CH$_2$).

EXAMPLE 4

5-(4-Fluorophenyl)-7-methyl-6-(4-pyridyl)-2,3-dihydro-1H-pyrrolizine

[3-(4-Fluorophenyl)-2-(4-pyridyl)-6,7-dihydro-5H-pyrrolizin-1-yl]methanol (3.08 g, 10 mmol) is heated with hydriodic acid (57%, 18 ml, 134 mmol HI) in an oil bath at 120° C. (reflux). The initially undissolved substance has dispersed in the batch after 45 min, and starting material (rf=0.05) is no longer detectable (product rf=0.9, iodide rf=0.6) by tlc (ether, Al$_2$O$_3$). After cooling (1 h), the solution is diluted with 50 ml of water and covered with a layer of 100 ml of ethyl acetate. The water phase is carefully neutralized with sat. Na$_2$CO$_3$ soln (30 ml) and the phases are separated. The water phase again extracted with ethyl acetate (50 ml), the combined ethyl acetate extracts decolorized using sodium thiosulfate solution (Na$_2$S$_2$O$_3$, 2% strength, 40 ml) and, after washing again with water (50 ml), dried over Na$_2$SO$_4$ sicc. After evaporating the solvent in vacuo, 2.28 g of residue remain, which solidifies from CH$_2$Cl$_2$/ethyl acetate to give a resinous mass. The substance is purified by CC (Al$_2$O$_3$/ether) and the substance obtained from the fractions by evaporating the solvent (fractions 1–17, 1.74 g) is crystallized from diisopropyl ether. 1.37 g of pure compound are obtained.

Yield: 47%; $C_{19}H_{17}FN_2$; MW=292.36

$^1$H-NMR (CDCl$_3$) δ[ppm]=8.45–8.41/7.07–7.03 (AA'BB'; 4H, -pyridyl); 7.17–6.93 (m; 4H, ar.); 3.945 (t; J=6.9 Hz, CH$_2$); 2.88 (t; J=7.2 Hz, CH$_2$); 2.51 (quin; J=7.0 Hz, CH$_2$); 2.10 (s; CH$_3$)

$^{13}$C-NMR (CDCl$_3$): δ[ppm]=164.2; 159.2; 149.5; 144.7; 135.5; 130.7; 130.6; 128.6; 128.5; 124.9; 124.6; 122.8; 115.7; 115.3; 108.4; 46.1; 27.2; 23.3; 10.5

EXAMPLE 5

5-(4-Fluorophenyl)-6-(4-pyridyl)-2,3-dihydro-1H-pyrrolizine

Ethyl 3-(4-fluorophenyl)-2-(4-pyridyl)-6,7-dihydro-5H-pyrrolizine-1-carboxylate (example 1A, 2.63 g, 7.5 mmol) is firstly dissolved at RT using hydriodic acid (57%, 7.5 ml, 56 mmol HI). The hydroiodide which has crystallized out again after a few minutes is brought into solution again by warming to 70° C. and the mixture is refluxed for 2 h. In this time, after about 45 min and after 1 h, in each case 2 further portions of HI (57%, a 3 ml, 45 mmol) are added. After passage of the reaction time, starting material (rf=0.4) is no longer detectable by tlc (Al$_2$O$_3$, ether-THF 9:1). For the isolation of the product (rf=0.55), the precipitate of the crystallized hydroiodide product formed on cooling is filtered off with suction, purified of adhering HI by washing with water (3 times 10 ml) and dried. 2.57 g of hydriodide (84.3%) are isolated.

Isolation of the Base:

5-(4-Fluorophenyl)-6-(4-pyridyl)-2,3-dihydro-1H-pyrrolizine hydriodide (3.68 g, 9 mmol) is suspended in $CH_2Cl_2$ (150 ml) and intensively stirred with saturated $NaHCO_3$ solution (100 ml). The $CH_2Cl_2$ phase is then separated off, dried using $Na_2SO_4$ sicc. and concentrated in vacuo. The residue is taken up in a little ether and the crystals formed are filtered off with suction and dried: 2.39 g.

Yield: 80%, $C_{18}H_{15}FN_2$; MW=278.33

IR (KBr): $1/\lambda$ ($cm^{-1}$)=1594, 1525, 1508, 1426, 1356, 1216, 833, 787;

$^1$H-NMR ($CDCl_3$) $\delta$[ppm]=8.38–8.35/7.11–7.09 (AA'BB'; 4H, -pyridyl); 7.31–7.24 (m; 2H, ar.); 7.11–7.02 (m; 2H, ar.); 6.15 (s; 1H); 3.89 (t; J=7.0 Hz, $CH_2$); 2.945 (t; J=7.2 Hz, $CH_2$); 2.51 (quin; J=7.0 Hz, $CH_2$);

$^{13}$C-NMR ($CDCl_3$): $\delta$[ppm]=160.0, 157.0, 149.2, 145.0, 137.7, 131.2, 131.1, 128.8, 122.0, 116.1, 115.6, 99.8, 45.9, 27.4, 24.5

EXAMPLE 6A

Ethyl 3-(2-thienyl)-2-(4-pyridyl)-6,7-dihydro-5H-pyrrolizine-1-carboxylate a) N-(2-Thienylcarbonyl)proline L-Proline (2.42 g, 21 mmol) is dissolved in NaOH (5%, 30 ml, 38 mmol) and the solution is cooled in an ice bath (5° C.). Thiophene-2-carbonyl chloride (2.93 g, 20 mmol) is slowly added dropwise with stirring (10–15 min), in the course of which the temperature should not exceed 7° C. The mixture is stirred at 5–7° C. for 1 h, the cooling is removed and stirring is continued for 1 h at RT. After acidifying the reaction mixture with HCl (10% strength, 12 ml) the amide deposits in oily form. The oil is extracted with ethyl acetate (300 ml), the ethyl acetate phase is washed a number of times with water (200 ml), dried ($Na_2SO_4$ sicc.) and the solvent is evaporated in vacuo.

The residue (4.16 g) is suspended twice using hot water (20 ml), filtered off with suction and washed with diisopropyl ether (10 ml). The substance is dried over $P_2O_5$ in vacuo (tlc: RP 18/MeOH, rf=0.75): 3.87 g.

M.p.: 143.0° C., yield: 81.6%; $C_{12}H_{12}FNO_3$; MW=237.23.

IR (KBr): $1/\lambda$ ($cm^{-1}$)=3091, 3078, 1717, 1601, 1524, 1439, 1406, 1262, 1240, 1195, 773, 757, 736;

$^1$H-NMR ($CDCl_3$:) $\delta$[ppm]=7.70 and 7.68 (d; J=3.7 Hz, 1H) 7.62 and 7.59 (d; J=5.0 Hz, 1H) 7.16–7.12 (dd; 1H) 4.85–4.79 (m; 1H) 3.94–3.87 (m; CH2) 2.50 (m; 1H) 2.12 (m; 3H);

b) Ethyl 3-(2-thienyl)-2-(4-pyridyl)-6,7-dihydro-5H-pyrrolizine-1-carboxylate

N-(2-Thienylcarbonyl)proline (4.69 g, 21 mmol) is dissolved in acetic anhydride (15 ml) at 60° C. (15 min), ethyl 2-bromo-3-(4-pyridyl)propenoate (6.40 g, 25 mmol) is added to the clear solution and the mixture is heated at 90° C. for 16 h, whereupon a tlc sample ($Al_2O_3$-ethyl acetate/THF 9:1) no longer indicates starting material. The cooled reaction mixture is treated with ethyl acetate (120 ml) and intensively stirred with saturated $Na_2CO_3$ solution (80 ml) for 15 min and diluted with water (50 ml). The ethyl acetate phase is separated off, the water phase is extracted with a further 3 portions of ethyl acetate (150 ml), and these organic phases are combined, washed with saturated $Na_2CO_3$ soln (50 ml) and, after drying ($K_2CO_3$ sicc.), concentrated in vacuo. 8 g are obtained as a residue, which is dissolved in a little ethyl acetate and purified by cc ($Al_2O_3$-ethyl acetate/n-hexane 2:1).

Fractions 6–12: contain the substance sought, which crystallizes from ether/diisopropyl ether, is filtered off with suction and dried: 2.63 g.

Yield: 37%, $C_{19}H_{18}N_2O_2S$, MW=338.43;

$^1$H-NMR ($CDCl_3$:) $\delta$[ppm]=8.52–8.49/7.23–7.20 (AA'BB'; 4H, -pyridyl and 1H; -thiophene); 6.925 (dd; J=3.6 Hz, 1H); 6.75 (d; J=3.5 Hz, 1H); 4.20–4.07 (m; 4H, $CH_2$); 3.23 (t; J=7.5 Hz, $CH_2$); 2.575 (quin; J=7.3 Hz, $CH_2$); 1.173 (t; J=7.1 Hz, $CH_3$)

Fractions 13–15: Mixed fraction with product from example 6B: 0.23 g

EXAMPLE 6B

Ethyl 3-(2-thienyl)-1-(4-pyridyl)-6,7-dihydro-5H-pyrrolizine-2-carboxylate

From CC purification of example 6A ($Al_2O_3$-ethyl acetate/n-hexane 2:1):

Fractions 19–30: contains the positional isomer compound, which likewise crystallizes in pure form from ether/diisopropyl ether, is filtered off with suction and dried: 0.19 g.

Fractions 31–end: contains compound 6B contaminated with N-(2-thienylcarbonyl)proline.

Yield: 2.7%, $C_{19}H_{18}N_2O_2S$, MW=338.43;

$^1$H-NMR ($CDCl_3$:) $\delta$[ppm]=8.56–8.53 (AA'BB'; 2H, -pyridyl); 7.43–7.40 (d; J=3.1 Hz, 1H, -thiophene); 7.30–7.29 (m; 3H, -pyridyl and -thiophene); 7.12–7.08 (dd; J=3.7 Hz, 1H); 4.15–3.99 (m; 4H, $CH_2$); 2.99 (t; J=7.3 Hz, $CH_2$); 2.53 (quin; J=7.2 Hz, $CH_2$); 1.035 (t; J=7.2 Hz, $CH_3$).

EXAMPLE 7

3-(2-Thienyl)-2-(4-pyridyl)-6,7-dihydro-5H-pyrrolizine-1-carboxylic acid

Analogously to Example 2

Ethyl 3-(2-thienyl)-2-(4-pyridyl)-6,7-dihydro-5H-pyrrolizine-1-carboxylate (example 6A, 1.5 g, 4.4 mmol) is stirred in ethanolic KOH (8%, 15 ml, 21 mmol) for 16 h at 60° C., the ethanol is evaporated in vacuo, and the residue is suspended in water (40 ml) and brought to pH4 in an ice bath using dil. $H_3PO_4$ (8%). The red-brown precipitate formed is filtered off with suction, washed with water and dried in vacuo. 1.17 g are obtained.

M.p.: dec.; yield: 85%; $C_{19}H_{15}FN_2O_2$; MW=322.34.

IR (KBr): $1/\lambda$ ($cm^{-1}$)=1676, 1604, 1567, 1420, 1305, 1196, 1012, 852, 702;

$^1$H-NMR ($CDCl_3$) $\delta$[ppm]=8.49–8.46/7.53–7.50 (AA'BB'; 4H, -pyridyl); 7.335 (d; J=3.1 Hz, 1H, -thiophene); 7.00 (d; J=3.7 Hz, 1H); 6.81 (dd, 1H, -thiophene); 4.79 (s, OH) 4.07 (t; J=7.1 Hz, $CH_2$); 3.28 (t; J=7.3 Hz, $CH_2$); 2.585 (m; $CH_2$).

EXAMPLE 8

5-(2-Thienyl)-6-(4-pyridyl)-2,3-dihydro-1H-pyrrolizine 3-(2-Thienyl)-2-(4-pyridyl)-6,7-dihydro-5H-pyrrolizine-1-carboxylic acid (example 7, 0.2 g, 0.64 mmol) is heated under argon in a 10 ml flask by immersing in a metal bath at 250° C. Evolution of $CO_2$ takes place immediately, and the substance melts and turns black. After cooling, the solidified, glassy melt is taken up in $CH_2Cl_2$ (10 ml) and filtered through $Al_2O_3$ (TSC, Baker). The filter cake is eluted with diethyl ether. The eluate is concentrated and crystallizes from ether/diisopropyl ether in the cold: white crystals 0.04 g.

Yield: 23%; $C_{16}H_{14}N_2S$; MW=266.37.

$^1$H-NMR ($CDCl_3$) $\delta$[ppm]=8.44–8.41/7.27–7.24 (AA'BB'; 4H, -pyridyl); 7.385 (dd, 1H, -thiophene); 7.07 (d; 2H, -thiophene); 6.99–6.97 (d; 1H, -thiophene); 6.16 (s; 1H); 3.955 (t; J=7.1 Hz, $CH_2$); 2.94 (t; J=7.3 Hz, $CH_2$); 2.52 (quin; J=7.2 Hz, $CH_2$).

EXAMPLE 9A
Ethyl 3-(5-chloro-2-thienyl)-2-(4-pyridyl)-6,7-dihydro-5H-pyrrolizine-1-carboxylate
a) (5-Chloro-2-thienylcarbonyl chloride 5-Chlorothiophene-2-carboxylic acid (4.0 g, 24.6 mmol) is dissolved in dichloroethane (10 ml) and thionyl chloride ($SOCl_2$, 2.7 ml, 4.4 g, 37 mmol) is added, after inoculating with a drop of DMF the batch is heated to 50° C. (IT). The course of the reaction is monitored by tlc ($SiO_2$/ether: product rf 0.8, starting material rf 0.1–0.3). After 1.5 h and after 2.5 h, in each case $SOCl_2$ (5 drops) was added. After 4.5 h, the pale yellow solution is concentrated on a Rotavapor and the residue is fractionally distilled: at 50 mbar 4.0 g of product (89.9%) is obtained at the distillation temperature of 110° C.

Yield: 4.0 g (90%); $C_5H_2Cl_2OS$; MW=181.04.

$^1$H-NMR ($CDCl_3$:) δ[ppm]=7.80/7.05 (AB; 2H, $J_{(AB)}$=4 Hz)

b) N-(5-Chloro-2-thienylcarbonyl)proline

5-Chlorothiophene-2-carbonyl chloride (3.62 g, 20 mmol) is slowly added dropwise with stirring (10–15 min) to a solution of L-proline (2.42 g, 21 mmol) in NaOH (5%, 32 ml, 40 mmol) cooled to 5° C. in an ice bath, the temperature not exceeding 9° C. The mixture is stirred at 5–7° C. for 30 min, in the course of which a precipitate slowly forms which is brought into solution again by addition of water (8 ml). The batch is stirred at RT for a further 90 min. After acidifying the reaction mixture with HCl (10% strength, 12 ml, pH 3.5), the amide deposits in crystalline form after stirring for 30 min. The crystals are filtered off with suction, washed a number of times with water (200 ml) and dried: crystallizate 1=2.61 g.

The mother liquor is acidified to pH 1–2 using HCl and the voluminous precipitate formed is likewise filtered off with suction and washed until neutral with water and dried: crystallizate 2: 2.17 g.

Both crystallizates are the substance sought: total yield 4.78 g.

Yield: 92%; $C_{10}H_{10}ClNO_3S$; MW=259.71.

$^1$H-NMR ($CDCl_3$:) δ[ppm]=8.50 (s; OH) 7.43/6.94 (AB; 2H, thiophene, $J_{(AB)}$=4 Hz); 4.77–4.72 (m; 1H); 3.91–3.77 (m; $CH_2$); 2.37–2.12 (m; 4H, $CH_2$).

c) Ethyl 3-(5-chloro-2-thienyl)-2-(4-pyridyl)-6,7-dihydro-5H-pyrrolizine-1-carboxylate N-(5-Chloro-2-thienylcarbonyl)proline (1.1 g, 4.2 mmol) is dissolved in acetic anhydride (3 ml) at 50° C. (IT) (15 min), ethyl 2-bromo-3-(4-pyridyl)propenoate (1.29 g, 5.0 mmol is added to the clear solution and the mixture is heated at 90° C. for 22 h, whereupon a tlc sample ($Al_2O_3$-ethyl acetate/THF 9:1) no longer indicates starting material.

The cooled reaction mixture is treated with ethyl acetate (50 ml) and water (50 ml) and intensively stirred for 15 min. The phases are separated, the water phase is treated to improve the phase separation with saturated NaCl solution (50 ml) and extracted with a further 3 portions of ethyl acetate (150 ml).

After this, the water phase is neutralized to pH 7–8 using saturated $Na_2CO_3$ soln (50 ml) and again extracted with ethyl acetate (50 ml).

The ethyl acetate phases are collected and combined, washed with saturated $Na_2CO_3$ soln (50 ml) and water (50 ml) and, after drying ($K_2CO_3$ sicc.), concentrated in vacuo. 1.2 g are obtained as a residue, which is dissolved in a little THF and purified by cc ($Al_2O_3$ (300 g)-ether/THF 9:1).

Fractions 1–30: contain the substance sought, which crystallizes from ether/diisopropyl ether, is filtered off with suction and dried: 0.6 g.

Yield: 38%, $C_{19}H_{17}ClN_2O_2S$, MW=372.88;

$^1$H-NMR ($CDCl_3$:) δ[ppm]=8.54–8.51/7.30–7.28 (AA'BB'; 4H, -pyridyl); 6.75/6.53 (AB; 2H, -thiophene, $J_{(AB)}$=4 Hz); 4.20–4.04 (m, 4H, $CH_2$); 3.22 (t; J=7.5 Hz, $CH_2$) 2.59 (quin; J=7.3 Hz, $CH_2$); 1.17 (t; J=7.1 Hz, $CH_3$).

EXAMPLE 9B
Ethyl 3-(5-chloro-2-thienyl)-1-(4-pyridyl)-6,7-dihydro-5H-pyrrolizine-2-carboxylate From CC purification of example 9A ($Al_2O_3$-ether/THF 9:1)

Fractions 35–60: contains the positional isomer compound, which likewise crystallizes in pure form from ether/diisopropyl ether, is filtered off with suction and dried: 0.11 g.

Yield: 1.5%, $C_{19}H_{17}ClN_2O_2S$, MW=372.88;

$^1$H-NMR ($CDCl_3$:) δ[ppm]=8.56–8.53/7.34–7.31 (AA'BB'; 4H, -pyridyl); 7.03/6.91 (AB; 2H, -thiophene, $J_{(AB)}$=4 Hz); 4.17–3.99 (q+t; 4H, $CH_2$); 3.00 (t; J=7.3 Hz, $CH_2$); 2.545 (quin; J=7.2 Hz, $CH_2$); 1.07 (t; J=7.1 Hz, $CH_3$).

EXAMPLE 10A
Ethyl 5-(4-fluorophenyl)-6-(4-pyridyl)-2,3-dihydropyrrolo-[2,1-b]-thiazole-7-carboxylate
a) Ethyl thiazolidine-2-carboxylate Ethyl glyoxalate (50% in toluene, 40.92 g, 0.2 mol), diluted with toluene (15 ml), is cooled to 5° C., cysteamine hydrochloride (22.72 g, 0.2 mol) is added and a saturated $NaHCO_3$ solution (8.7% strength, 120 ml) is slowly added dropwise (2 h). The temperature is kept below 15° C. during the dropwise addition.

The 2-phase system is stirred at RT for 16 h.

The reaction is checked by means of GC: HP17, 10 m, 0.53 mm; Temp.: 120° C. (0.5 min), 20° C./min, 180° C. (1 min), inj 220° C., det. 280° C.; rt 2.57.

After this, the toluene phase is separated off and the aqueous phase (pH 7–8) is extracted with ether (150 ml). Toluene phase and ether phase are dried over $Na_2SO_4$ (sicc.) and concentrated and the oily residues are purified: 26.9 g.

Yield (crude): 83.5%, $C_6H_{11}NO_2S$, 161.22 g/mol;

IR (KBr): $1/\lambda$ (cm$^{-1}$)=3303, 2980, 2939, 1733, 1672, 1516, 1443, 1369, 1282, 1182, 1026;

$^1$H-NMR ($CDCl_3$:) δ[ppm]=4.92 (s,1H); 4.25 (q, 2H, J=7.1 Hz); 3.66 (m, 1H); 3.10–2.95 (m, 2H); 2.90–2.78 (m, 1H); 2.44 (s, OH); 1.305 (t, 3H, J=7.1 Hz)

b) Ethyl 3-(4-fluorobenzoyl)thiazolidinecarboxylate

The solution of ethyl thiazolidine-2-carboxylate (24.18 g, 0.15 mol) in abs. $CH_2Cl_2$ (80 ml) is treated dropwise at RT with the solution of 4-fluorobenzoyl chloride (23.78, 0.15 mol) in abs. $CH_2Cl_2$ (20 ml). The solution warms to 38° C., the solvent begins to boil and HCl is released. It is kept under reflux for 4 h with heating.

The $CH_2Cl_2$ phase is extracted by stirring (30 min) with $Na_2CO_3$ soln (100 ml), washed with water (50 ml) and separated off. It is dried over $Na_2SO_4$ (sicc.) and concentrated. The residue which remains is crystallized from diisopropyl ether (30 ml), and the crystals are washed with diisopropyl ether (25 ml) and dried: 34.07 g.

Yield: 80.2%, $C_{13}H_{14}FNO_3S$, MW=283.32;

$^1$H-NMR ($CDCl_3$:) δ[ppm]=7.52 (m; 2H, ar.); 7.17–7.05 (m; 2H, ar.); 4.30–4.20 (q; J=7.1 Hz, $CH_2$); 3.98–3.87 (m; $CH_2$); 3.32–3.19 (m; 1H); 3.09–2.98 (m; 1H); 1.305 (t; J=7.1 Hz, $CH_3$).

c) 3-(4-Fluorobenzoyl)thiazolidinecarboxylic acid

Ethyl 3-(4-fluorobenzoyl)thiazolidinecarboxylate (28.33 g, 0.1 mol) is suspended in ethanolic KOH (5% strength, 165 ml, 0.15 mol) and the mixture is subsequently heated at 50° C. (IT) for 2 h. The cooled solution is acidified (pH 2–3) with water (100 ml) and dil. phosphoric acid (8%, 150 ml).

Precipitated salts are brought into solution again by addition of water (150 ml). This aqueous solution is extracted with diethyl ether (500 ml), the ethereal extracts are washed with sat. NaCl solution (100 ml), dried over $Na_2SO_4$ (sicc.) and concentrated in vacuo. The residue is crystallized from diisopropyl ether (40 ml): 24.87 g.

Yield: 97.5%, $C_{11}H_{10}FNO_3S$, MW=255.27;

$^1$H-NMR (CDCl$_3$:) δ[ppm]=8.64 (s; 1H, OH); 7.59–7.53 (m; 2H, ar.); 7.19–7.09 (m; 2H, ar.); 5.64 (S; CH); 3.98–3.92 (m; CH$_2$); 3.36–3.24 (m; CH$_2$); 3.11–3.01 (m; CH$_2$).

d) Ethyl 5-(4-fluorophenyl)-6-(4-pyridyl)-2,3-dihydropyrrolo-[2,1-b]-thiazole-7-carboxylate The clear solution of 3-(4-fluorobenzoyl)thiazolidinecarboxylate (12.76 g, 0.05 mol) in acetic anhydride (60 ml) obtained at 90° C. is treated with ethyl 2-bromo-3-(4-pyridyl)propenoate (13.8 g, 54 mmol) and stirred at 80° C. (IT) for 4 d. The black-colored reaction mixture is concentrated in vacuo and, after cooling, treated with MeOH (10 ml). After the reaction is complete, residual acetic anhydride is again concentrated in vacuo and the residue (30 g) is dissolved completely in MeOH (7 ml) in the presence of heat. Product 10 A crystallizes at RT (TLC: Al$_2$O$_3$, ethyl acetate/n-hexane 6:4; rf=0.45). The crystal magma is filtered off with suction, the crystals are collected (2.6 g) and the mother liquor is placed in the cold (0° C.) to obtain a further crystal fraction (2.16 g): 4.42 g (24%)

After filtration, the mother liquor is diluted with CH$_2$Cl$_2$ (20 ml) and filtered through a little Al$_2$O$_3$. The Al$_2$O$_3$ is washed with CH$_2$Cl$_2$ (150 ml) and the eluates are concentrated: 5.78 g (mixture of product A, rf=0.45 and B, rf=0.5).

The yellow-colored crystals of the two crystal fractions are washed with a little cold MeOH and dried:

Yield: 24%, $C_{20}H_{17}FN_2O_2S$, MW=368.43;

IR (KBr): 1/λ (cm$^{-1}$)=3066, 2992, 2786, 1722, 1692, 1627, 1520, 1377, 1226, 1147, 820, 596;

$^1$H-NMR (CDCl$_3$:) δ[ppm]=8.57–8.55/7.33–7.30 (AA'BB'; 4H, -pyridyl); 7.47–7.40 (m; 2H, ar.); 7.18–7.10 (m; 2H, ar.); 4.11–3.99 (q+t; 4H, CH$_2$); 3.69 (t; J=7.0 Hz, CH$_2$); 0.98 (t; J=7.1 Hz, CH$_3$).

EXAMPLE 10B
Ethyl 5-(4-fluorophenyl)-7-(4-pyridyl)-2,3-dihydropyrrolo-[2,1-b]-thiazole-6-carboxylate From the mixture (5.78 g) of product A (rf=0.45) and B (rf=0.5) obtained under example 10 A, small fractions of pure product 10 B are obtained by CC on Al$_2$O$_3$ using the eluent ethyl acetate/n-hexane (6:4):

$C_{20}H_{17}FN_2O_2S$, MW=368.43;

$^1$H-NMR (CDCl$_3$:) δ[ppm]=8.44–8.41/7.36–7.33 (AA'BB'; 4H, ar.); 7.11–7.00 (m; 4H, ar.); 4.28–4.15 (m; 4H); 3.77–3.70 (m; 2H); 1.275 (t; CH$_3$, J=7.1 Hz).

EXAMPLE 11
5-(4-Fluorophenyl)-6-(4-pyridyl)-2,3-dihydro-pyrrole-[2,1-b]-thiazole-7-carboxylic acid The compound of example 10 A (1.0 g, 2.7 mmol) is cleaved completely (tlc) in 4 h by boiling under reflux in ethanolic KOH (10%, 10 ml, 18 mmol). The ethanolic liquor is concentrated in vacuo, the salt-like residue is taken up in water (40 ml) and the excess of alkali is neutralized (pH 4–5) using H$_3$PO$_4$ (8%) to the extent that the suspension does not assume a gelatinous consistency. The solid is filtered off with suction, washed with water and dried over P$_2$O$_5$ in an evacuated desiccator for 24 h: 0.87 g of pale yellow powder M.p. 210.5° C., yield: 94.6%; $C_{18}H_{13}FN_2O_2S$, MW=340.38;

IR (KBr): 1/λ (cm$^{-1}$)=3399, 1672, 1599, 1534, 1494, 1228, 1160.

$^1$H-NMR (d$_6$-DMSO/CDCl$_3$): δ[ppm]=8.55–8.52/7.91–7.87 (AA'BB'; 2H, -pyridyl); 7.50–7.43 (m, 2H); 7.19–7.10 (m, 2H); 4.14 (t; J=7.1 Hz, CH$_2$); 3.83 (t; J=7.2 Hz, CH$_2$);

$^{13}$C-NMR (d$_6$-DMSO/CDCl$_3$): δ[ppm]=165.3, 164.6, 159.7, 148.5, 142.7, 140.2, 134.6, 131.5, 131.4, 130.5, 127.22, 127.15, 122.8, 114.8, 114.4, 47.3, 34.4.

EXAMPLE 12
[5-(4-Fluorophenyl)-6-(4-pyridyl)-2,3-dihydro-pyrrolo-[2,1-b]-thiazol-7-yl]methanol The compound of example 10 A (0.37 g, 1.0 mmol) is dissolved in abs. THF (7 ml) at 50° C. and kept at 55° C. for 7 h with a solution of Na bismethoxyethoxyaluminum hydride in toluene (Vitride$^R$, 70% strength, 0.80 ml, 2.8 mmol). After cooling, the excess of hydride is decomposed in an ice bath using a little water and the suspension is stirred until formation of the precipitate is complete. The precipitate is filtered off with suction and washed with water until the reaction of the wash phase is neutral: 0.27 g.

Yield: 82%, $C_{18}H_{15}FN_2OS$, MW=326.40;

$^1$H-NMR (DMSO-d$_6$/CDCl$_3$): δ[ppm]=8.76–8.55/7.59–7.55 (AA'BB'; 4H, -pyridyl); 7.51–7.44 (m; 2H, ar.); 7.20–7.11 (m; 2H, ar.); 4.49 (s; CH$_2$); 4.17 (t; J=7.0 Hz, CH$_2$); 3.73 (t; J=7.0 Hz, CH$_2$).

EXAMPLE 13
5-(4-Fluorophenyl)-7-methyl-6-pyridin-4-yl-2,3-dihydropyrrolo-[2,1-b]-thiazole The compound of example 12 (2.05 g, 6.3 mmol) is brought into solution in a mixture of abs. acetonitrile (16 ml), glacial acetic acid (1.6 ml) and a little abs. DMF at 50° C., sodium iodide (2.35 g, 15.7 mmol) is added and then trimethylsilyl chloride (TMSCl, 1.6 ml, 1.37 g, 12.7 mmol) is added dropwise. The temperature of the batch is kept at 50° C. for 2 h. Glacial acetic acid (1.6 ml) and zinc powder (2.87 g, 44 mmol) is added in three portions and the mixture is stirred at 80° C. for 16 h. The mixture is cooled, treated with a little water and extracted with CH$_2$Cl$_2$. The CH$_2$Cl$_2$ extracts are dried over Na$_2$SO$_4$ sicc. and concentrated. The residue obtained is taken up in THF and eluted through Al$_2$O$_3$ (50 g) using THF. From the residue (1.4 g) obtained after evaporation of the THF, using acetone 0.6 g of pale yellow substance (94%; HPLC: RP 18; acetonitrile/NaH$_2$PO$_4$ buffer 70:30) is obtained, which is recrystallized from MeOH in the presence of heat: 0.43 g of pale yellow powder.

M.p. 208° C.; yield: 23%, $C_{18}H_{15}FN_2S$, MW=310.4;

IR (KBr): 1/λ (cm$^{-1}$)=1596, 1557, 1533, 1499, 1420, 1361, 1303, 1226, 1158, 1098, 1053, 989, 852, 822, 735, 721, 529;

$^1$H-NMR (CDCl$_3$): δ[ppm]=8.57 (2H, -pyridyl); 7.35–7.27(m; 4H, -pyridyl and ar.); 7.19–7.10 (m; 2H, ar.); 4.12 (t; J=7.0 Hz, CH$_2$); 3.72 (t; J=7.0 Hz, CH$_2$); 2.23 (s; CH$_3$).

$^{13}$C-NMR (d$_6$-DMSO/CDCl$_3$): δ[ppm]=164.6, 159.7, 147.7, 145.2, 132.6, 131.0, 130.8, 129.8, 127.5, 121.4, 119.4, 116.0, 115.6, 113.3, 47.9, 35.3, 12.8.

EXAMPLE 14
5-(4-Fluorophenyl)-6-pyridin-4-yl-2,3-dihydro-pyrrolo-[2,1-b]-thiazole 5-(4-Fluorophenyl)-6-(4-pyridyl)-2,3-dihydropyrrolo-[2,1-b]-thiazole-7-carboxylic acid (example 11, 120 mg, 0.35 mmol) is heated under argon in an oil bath firstly at 140° C. for 2 h and then at 180° C. for 3 h. After cooling to RT, the brown-red melt cake is digested with a little EtOH. The undissolved, red-brown substance is filtered off with suction, washed with ether and dried: 0.07 g.

Yield: 67%, $C_{17}H_{13}FN_2S$, MW=296.37;
$^1$H-NMR (CDCl$_3$): δ[ppm]=8.46–8.43/7.64–7.61 (AA'BB'; 4H, -pyridyl); 7.44–7.37 (m; 2H, ar.); 7.20–7.11 (m; 2H, ar.); 6.67 (s; CH); 4.35 (t; J=7.2 Hz, CH$_2$); 3.95 (t; J=7.2 Hz, CH$_2$).

EXAMPLE 15A

Ethyl 3-(4-fluorophenyl)-2-(4-pyridyl)-5,6,7,8-tetrahydroindolizine-1-carboxylate a) 1-(4-Fluorobenzoyl)piperidine-2-carboxylic acid D,L-Pipecolic acid (16.15 g, 0.125 mol), dissolved in NaOH (5%, 200 ml, 0.25 mol) is treated dropwise at 5° C. (ice-bath cooling) with 4-fluorobenzoyl chloride (19.83 g, 0.125 mol), and the magma forming after 1 h is liquefied using water (50 ml) before further acid chloride addition. The batch is stirred at 10–15° C. for 4 h.

By addition of water (220 ml), the precipitate formed is almost completely brought into solution (pH=8–9) and using ether (160 ml) the radicals of the acid chloride and other neutral impurities are removed. The desired product is deposited from the alkaline water phase by addition of HCl (10% strength) until pH 2 is reached. The HCl-acidic suspension is extracted with ether (300 ml), and the ether phase is separated off, dried (Na$_2$SO$_4$ sicc.) and concentrated in vacuo. The residue (8% 4-fluorobenzoic acid) is crystallized from ether (20 ml): 28.67 g.

Yield: 72%, $C_{13}H_{14}FNO_3$, MW=251.3;
$^1$H-NMR (CDCl$_3$): δ[ppm]=8.30 (br; 1H, OH); 7.50–7.35 (m; 2H, ar.); 7.20–7.00 (m; 2H, ar.); 5.50 (m; 1H, CH$_X$N); 4.70–4.4 (m; 1H, CH$_A$H$_B$); 3.75–3.60 (m; 1H, CH$_A$H$_B$); 3.35–3.15 (m; 1H, CH$_A$H$_B$); 2.45–2.30 (m; 1H, CH$_A$H$_B$); 1.9–1.3 (m; 4H, CH$_A$H$_B$).

b) Ethyl 3-(4-fluorophenyl)-2-(4-pyridyl)-5,6,7,8-tetrahydroindolizine-1-carboxylate 1-(4-Fluorobenzoyl)piperidine-2-carboxylic acid (17.6 g, 0.07 mol) is dissolved in acetic anhydride (45 ml) at 80° C. and then ethyl 2-bromo-3-(4-pyridyl)propenoate (22.4 g, 0.087 mol). A strong evolution of CO$_2$ is ended after about 10 min. The reaction mixture is kept at 130° C. (reflux) for 20 h. After cooling, CH$_2$Cl$_2$ (100 ml) and water (50 ml) are added and the mixture is vigorously stirred for 10 min, then the phases are separated. The water phase is extracted again with CH$_2$Cl$_2$ (150 ml), and the combined organic phases are washed until neutral with sat. Na$_2$CO$_3$ soln (50 ml), dried (Na$_2$SO$_4$ sicc.) and concentrated. 29.26 g of crude product remain. The acidic water phase is alkalized with NaOH, black lumps depositing which are partly soluble in CH$_2$Cl$_2$ (200 ml) and contain residues of the compound sought.

Residue of this CH$_2$Cl$_2$ phase and crude product fraction are combined (30 g), taken up in CH$_2$Cl$_2$ (30 ml) and purified by cc on Al$_2$O$_3$ (2300 g) using ether/THF (9:1):

Fractions 4–12: 12.5 g of product 15 A, which crystallizes from diisopropyl ether/n-hexane (10 ml, 1:1). The crystals are filtered off with suction and dried: 9.3 g (36.6%).

Yield: 9.3 g (36.6%) $C_{22}H_{21}FN_2O_2$; MW=364.42.
$^1$H-NMR (CDCl$_3$) δ[ppm]: 8.39–8.36/7.04–7.02 (AA'BB'; 4H, -pyridyl); 7.13–6.93 (m; 4H, ar.); 4.12 (q; J=7.11 Hz, CH$_2$); 3.705 (t; J=3 Hz, CH$_2$); 3.21 (t; J=2 Hz, CH$_2$); 1.98–1.85 (m, 2 CH$_2$, 4H); 1.09 (t; J=7.1 Hz, CH$_3$).

EXAMPLE 15B

Ethyl 3-(4-fluorophenyl)-1-(4-pyridyl)-5,6,7,8-tetrahydroindolizine-2-carboxylate CC purification of the compound from example 15A, b) Separation on Al$_2$O$_3$— ether/THF 9:1: fractions 13–19: 2.35 g of substance 15B.

Crystals from diisopropyl ether/n-hexane (1 ml, 1:1): 1.66 g.

Yield: 6.6%; $C_{22}H_{21}FN_2O_2$; MW=364.42.
$^1$H-NMR (d6-DMSO) δ[ppm]=: 8.50–8.45 (AA', 2 H, pyridinyl); 7.45–7.37 (m, 2H, ar.); 7.30–7.15 (m, 4H, ar.+ BB' pyridinyl); 3.80 (q, 2H, J=7.0 Hz, OCH2); 3.65–3.55 (m, 2H, CH$_2$); 2.75–2.65 (m, 2H CH$_2$); 1.80–1.60 (m, 4H, CH$_2$—CH$_2$) 0.757 (t, 3H, J=7.0 Hz, CH$_3$).
$^{13}$C-NMR (CDCl$_3$): δ[ppm]=164.10, 162.09 (d, J=243.4 Hz), 148.80, 143.29, 135.61, 132.840 (d, J=8.4 Hz), 128.58, 127.816 (d, J=3.3 Hz), 124.91, 117.61, 114.91 (d, J=21.4 Hz), 111.33, 58.96, 44.35, 22.71, 22.34, 19.93, 13.52.

EXAMPLE 16

[3-(4-Fluorophenyl)-2-(4-pyridyl)-5,6,7,8-tetrahydroindolizine-1-yl]methanol

The solution of ethyl 3-(4-fluorophenyl)-2-(4-pyridyl)-5,6,7,8-tetrahydroindolizine-1-carboxylate (example 15 A, 2.55 g, 7 mmol) in abs. THF (15 ml) is treated dropwise under argon at RT with the solution of NaAlH$_2$(OC$_2$H$_4$OCH$_3$)$_2$ in toluene (Vitride$^R$ 70%, 2.9 ml, 10 mmol) and the batch is stirred at 40° C. for 24 h until the complete disappearance of the starting material (tlc Al$_2$O$_3$/ethyl acetate: starting material rf=0.8; product rf=0.5). The excess of hydride is destroyed by addition of water (2 ml), then THF is removed in vacuo and the residue is taken up in ethyl acetate. The ethyl acetate phase is washed with water until the reaction of the wash phases is neutral (60 ml). The ethyl acetate phase is dried over Na$_2$SO$_4$ sicc. and concentrated: a residue of 2.15 g remains.

Yield: 95%; $C_{20}H_{19}FN_2O$; MW=322.4.
IR (KBr): 1/λ (cm$^{-1}$)=3243, 2946, 1600, 1534, 1511, 1221, 994, 840, 579;
$^1$H-NMR (CDCl$_3$) δ[ppm]=8.40–8.37/7.15–7.12 (AA'BB'; 4H, -pyridyl); 7.17–7.12 (m; 2H, ar.); 7.07–6.98 (m; 2H, ar.); 4.55 (s; CH$_2$); 3.80–3.70 (m; CH$_2$); 3.00–2.90 (m; CH$_2$); 1.95–1.90 (m; 4H, CH$_2$).

EXAMPLE 17

3-(4-Fluorophenyl)-1-methyl-2-(4-pyridyl)-5,6,7,8-tetrahydroindolizine

The mixture of [3-(4-fluorophenyl)-2-(4-pyridyl)-5,6,7,8-tetrahydroindolizin-1-yl]methanol (example 16, 3.52 g, 11 mmol) with hydriodic acid (57%, 20 ml, 0.15 mol) is heated to 100° C. and the course of the reaction is checked by tlc (Al$_2$O$_3$, ether). After 45 min, starting material (rf=0.2) is no longer detectable (product: rf=0.7).

The cooled reaction mixture is treated with ethyl acetate (100 ml), extracted by shaking with sat. Na$_2$CO$_3$ solution and decolorized using Na$_2$S$_2$O$_3$ solution and then washed with water. The ethyl acetate phase is dried over Na$_2$SO$_4$ sicc. and concentrated. The residue is purified by cc (Al$_2$O$_3$, ether/THF 9:1): fraction 4–11 yields 1.6 g of product, which crystallizes from diisopropyl ether: 1.02 g Yield: 30.4%; $C_{20}H_{19}FN_2$; MW=306.4.
$^1$H-NMR (CDCl$_3$) δ[ppm]=8.40–8.36/7.00–6.97 (AA'BB', 4H, -pyridyl); 7.18–7.11 (m; 2H, ar.); 7.04–6.96 (m; 2H, ar.); 3.75–3.70 (m; CH$_2$); 2.83–2.78 (m; CH$_2$); 2.08 (S; 3H, CH$_3$); 1.95–1.85 (m; 4H, CH$_2$—CH$_2$);
$^{13}$C-NMR (CDCl$_3$): δ[ppm]=164.5, 159.6, 149.1, 144.5, 132.6, 132.4, 128.6, 128.2, 128.1, 126.9, 124.6, 119.9, 115.7, 115.3, 11.9, 44.4, 23.8, 22.0, 20.9.

EXAMPLE 18

3-(4-Fluorophenyl)-2-(4-pyridyl)-5,6,7,8-tetrahydroindolizine

Ethyl 3-(4-fluorophenyl)-2-(4-pyridyl)-5,6,7,8-tetrahydroindolizine-1-carboxylate (example 15A, 2.92 g, 8 mmol) and hydriodic acid (57%, 16.0 ml, 27 g, 120 mmol) are mixed at 60° C. and maintained at a temperature of 120°

C. The initially deposited hydriodide dissolves again in the presence of heat (10 min). The course of the reaction is checked by tlc ($Al_2O_3$, ether/THF 9:1). After 30 min, the conversion is complete (starting material rf=0.6; product rf=0.8). The mixture is cooled in an ice bath.

The precipitate of the crystallized hydriodide formed is filtered off with suction, purified of adherent HI by washing with water (6 times 5 ml) and dried in vacuo (desiccator, $P_2O_5$). 2.68 g (79.5%) of hydriodide are isolated.

The mother liquor of the crystallization is neutralized using NaOH and extracted with ethyl acetate. The ethyl acetate phase is decolorized using $Na_2S_2O_3$ solution and then washed with water. The ethyl acetate phase is dried over $Na_2SO_4$ sicc. and concentrated: 0.44 g of product (base).
Isolation of the Base 5-(4-Fluorophenyl)-6-(4-pyridyl)-2,3-dihydro-1H-pyrrolizine hydriodide (2.68 g, 9.2 mmol) is suspended in $CH_2Cl_2$ (150 ml) and intensively stirred with saturated $NaHCO_3$ solution (40 ml). The $CH_2Cl_2$ phase is then separated off, dried using $Na_2SO_4$ sicc. and concentrated in vacuo to a small volume (5 ml). The crystals formed are washed with diisopropyl ether and dried: 1.66 g.

Yield: 72.2%, $C_{19}H_{17}FN_2$; MW=292.36

$^1$H-NMR (CDCl$_3$) δ[ppm]=8.32–8.29/7.01–6.98 (AA'BB', 4H, -pyridyl); 7.30–7.21 (m; 2H, ar.); 7.16–7.06 (m; 2H, ar.); 6.21(s; 1H); 3.70–3.64(m, $CH_2$); 2.91–2.85 (m; $CH_2$); 1.98–1.80 (m; 4H, $CH_2$—$CH_2$);

$^{13}$C-NMR (CDCl$_3$): δ[ppm]=165.0, 160.1, 149.3, 144.2, 132.8, 132.6, 130.4, 126.1, 128.5, 128.4, 121.6, 119.2, 116.1, 115.7, 104.2, 44.3, 23.6, 23.4, 20.9.

EXAMPLE 19A
Ethyl 2-(4-fluorophenyl)-3-(4-pyridyl)-6,7-dihydro-5H-pyrrolizine-1-carboxylate a) Benzyl 1-(pyridine-4-carbonyl)pyrrolidine-2-carboxylate L-Proline benzyl ester hydrochloride (2.42 g, 0.01 mol) dissolved in pyridine (80 ml) is treated in portions at 3° C. (ice-bath cooling) with isonicotinoyl chloride hydrochloride (1.78 g, 0.01 mol), the IT increasing to 10° C. After removing the ice bath, the mixture is stirred for 5 h, the batch turning greenish.

Excess pyridine is removed on a Rotavapor and the residue obtained is partitioned between water (40 ml) and ether. After separating off the ether phase, the water phase is extracted with ether (60 ml). The ether phases are collected, washed with water (20 ml), dried ($Na_2SO_4$ sicc.) and concentrated in vacuo. The residue is dried in a high vacuum: 2.96 g.

Yield: 85%, $C_{18}H_{18}N_2O_3$, MW=310.36;

$^1$H-NMR (CDCl$_3$): δ[ppm]=8.72–8.69/7.43–7.40 (AA'BB', 4H, -pyridyl); 7.37 (s; 5H); 5.260/5.188 (AB, $J_{AB}$=12.3 Hz, OCH$_2$Ph); 4.765–4.695 (m, CH$_X$, 1H); 3.610–3.395 (m, 2H, CH$_A$H$_B$); 2.140–1.875 (m, 4H, C$\underline{H}_2$—C$\underline{H}_A$H$_B$—CH$_X$).

b) 1-(Pyridine-4-carbonyl)pyrrolidine-2-carboxylic acid

Benzyl 1-(pyridine-4-carbonyl)pyrrolidine-2-carboxylate (4.0 g, 11.5 mmol) is dissolved at RT in a mixture of THF and ethanol abs. (1:1, 30 ml), and treated with palladium on active carbon (10%, 0.7 g). Evacuation is then carried out three times and the vacuum is replaced by hydrogen from a balloon.

The mixture we hydrogenated at atm and RT for 16 h. After this, the reaction mixture no longer contains starting material (tlc $Al_2O_3$/n-hexane ethyl acetate (1:1); starting material: rf=0.2–0.4 and product: rf=0.0).

The product solution is removed from the catalyst (G4), concentrated in vacuo and dried in a high vacuum, 2.95 g (>100%), content according to gc about 60% strength.

c) Ethyl 2-bromo-3-(4-fluorophenyl)propenoate

With exclusion of light, bromocarbethoxymethylenetriphenyl-phosporane (example 1A, b; 9.0 g, 21 mmol) is brought into solution in toluene (60 ml) and and the solution of 4-fluorobenzaldehyde (2.48 g, 20 mmol) in toluene (9 ml) is then added. The solution is stirred at RT for 16 h in the dark, concentrated in vacuo, the residue is treated with ether (40 ml) and the crystals deposited in the course of this are washed with ether (2×10 ml).

The collected ether solutions are concentrated in vacuo and the residue which remains (7.82 g) is treated with an ether/n-hexane mixture (1:1, 5 ml). Precipitate remaining undissolved during this is separated off and washed with ether/n-hexane mixture (1:1). On concentrating, 6.06 g of the residue still remain here which are purified by cc (SiO$_2$, ether/n-hexane 1:1): The substance sought appears in the fractions 1–2: yellow-brown oil, 4.72 g.

Yield: 99. 6%; $C_{11}H_{10}BrFO_2$; MW=273.10.;

IR (NaCl): 1/λ (cm$^{-1}$)=2983, 1724, 1601, 1508, 1261, 1235, 1195, 1161, 1040, 833;

$^1$H-NMR (CDCl$_3$:) δ[ppm]=8.18 (s; 1H); 7.91–7.84 (m, 2H, ar.); 7.16–7.07 (m; 2H, ar.) 4.36 (q; J=7.2 Hz, CH$_2$); 1.38 (t; J=7.1 Hz, CH$_3$);

$^{13}$C-NMR (CDCl$_3$:) δ[ppm]=163.4 (d, J=250 Hz), 163.2, 139.4, 138.7, 132.4 (d, J=9 Hz), 129.9, 115.55 (d, 24 Hz), 112.9, 62.7, 15.1.

d) Ethyl 2-(4-fluorophenyl)-3-(4-pyridyl)-6,7-dihydro-5H-pyrrolizine-1-carboxylate A mixture of 1-(pyridine-4-carbonyl)pyrrolidine-2-carboxylic acid (example 19A, b; 60%, 1.5 g, 4.1 mmol), ethyl 2-bromo-3-(4-fluorophenyl)propenoate (example 19A, c; 1.0 g, 4 mmol) and acetic anhydride (10 ml) are heated under reflux for 21 h in an oil bath maintained at a temperature of 150° C. After cooling and concentrating in vacuo (Rotavapor), needles deposit. The concentrated crystal suspension is treated with ether/ethyl acetate (1:2) and the crystals are filtered off with suction. The mother liquor is completely concentrated and the residue is purified by cc ($Al_2O_3$— ether/THF 9:1):

Fractions 3–5: product 19 A, which crystallizes from ether.

The crystals are filtered off with suction and dried: 0.12 g.
Yield: 8.5%, $C_{21}H_{19}FN_2O_2$; MW=350.4.

$^1$H-NMR (CDCl$_3$) δ[ppm]=8.45–8.42/6.97–6.94 (AA'BB'; 4H, -pyridyl); 7.23–7.15/7.02–6.93 (AA'BB'; 4H, ar.); 4.20–4.09 (q, CH$_2$O;+t, CH$_2$, 4H); 3.23 (t; J=7.5 Hz, 2H); 2.58 (quin; J=7.2 Hz, 2H, CH$_2$); 1.18 (t; J=7.1 Hz, CH$_3$)

EXAMPLE 19B
Ethyl 1-(4-fluorophenyl)-3-(4-pyridyl)-6,7-dihydro-5H-pyrrolizine-2-carboxylate CC purification of the compound from example 19A, d) Separation on $Al_2O_3$-ether/THF 9:1: fractions 7–20, crystals from ether: 0.05 g.

Yield: 3%; $C_{21}H_{19}FN_2O_2$; MW=350.4.

$^1$H-NMR (CDCl$_3$) δ[ppm]=8.67–8.64/7.40–7.37 (AA'BB'; 4H, pyridyl); 7.39–7.32/6.98–6.93 (m; 4H, ar.); 3.97 (t; 2H, J=7.1 Hz); 2.94 (t; 2H, J=7.2 HZ); 2.62–2.48 (m; 2H); 0.975 (t; J=7.1 Hz, CH$_3$).

EXAMPLE 20
[2-(4-Fluorophenyl)-3-(4-pyridyl)-6,7-dihydro-5H-pyrrolizin-1-yl]methanol Ethyl 2-(4-fluorophenyl)-3-(4-pyridyl)-6,7-dihydro-5H-pyrrolizine-1-carboxylate (example 19A, 0.15 g, 0.43 mmol) is dissolved under argon in abs. THF (4 ml) and sodium dihydrido-bis(2-methoxy-ethoxy)aluminate solution (Vitride$^R$, 70% in toluene, 0.9 ml, 4.5 mmol) is added dropwise in 4 portions at 40° C. with exclusion of moisture at in each case an interval of 1 hour. 1 h after the last addition, starting material can no longer be detected by tlc (Al$_2$O$_3$— ethyl acetate/n-hexane 3:7).

After this, the mixture is allowed to cool. The reaction solution is partitioned between water (20 ml) and ethyl acetate (20 ml) and the water phase is neutralized to pH 6–7 by means of HCl (3%). The phases are separated and the water phase is extracted 3 times by shaking with ethyl acetate (20 ml). The combined organic phase is dried over Na$_2$SO$_4$ sicc and concentrated in vacuo: 0.21 g.

Yield: >100%; C$_{19}$H$_{17}$FN$_2$O; MW=308.36.

$^1$H-NMR (CDCl$_3$): δ[ppm]=8.41–8.38/7.05–7.01 (AA'BB'; 4H, -pyridyl); 7.26–7.20 (m; 2H, ar.); 7.04–6.97 (m; 2H, ar.); 4.47 (S; CH$_2$O); 4.12 (t; J=7.0 Hz, CH$_2$N); 3.01 (t; J=7.3 Hz, CH$_2$); 2.57 (quin; J=7.5 Hz, 2H, CH$_2$).

EXAMPLE 21

6-(4-Fluorophenyl)-7-methyl-5-(4-pyridyl)-2,3-dihydro-1H-pyrrolizine a) 2-Ethyl-1-pyrroline Sodium hydride (60% in paraffin, 36 g, 0.9 mol) in abs. THF (180 ml) is suspended in a 1 l 3-necked flask having a dropping funnel and reflux condenser and the suspension is heated with gentle refluxing for 10 min. The mixture of ethyl propionate (33.7 g, 0.33 mol) and 1-vinyl-2-pyrrolidone (33.34 g, 0.3 mol) in abs. THF (35 ml) are added dropwise to the boiling suspension (10 min) and kept under reflux by heating for 3.5 h with stirring.

After cooling to 10° C. (ice bath) the excess of sodium hydride is destroyed and neutralized using sat. ammonium chloride solution (300 ml) (beware! H$_2$) and to drive off the ammonia liberated the now warm mixture (30° C.) is intensively stirred for a further 10 min. The deposited THF phase is separated off, dried over Na$_2$SO$_4$ sicc. and concentrated. The paraffin layer depositing on the oil phase is decanted. The red, oily product fraction obtained (3-propionyl-1-vinyl-2-pyrrolidone, 51.2 g, about 92%) is used without further purification for the preparation of 2-ethyl-1-pyrroline:

B.p.=140.20° C. (760 torr), yield: 102%, C$_9$H$_{13}$NO$_2$, MW=167.21.

IR (NaCl): 1/λ (cm$^{-1}$)=2955, 2925, 2854, 1698, 1633, 1456, 1427, 1387, 1327, 1273, 1114, 979;

$^1$HNMR (CDCl$_3$): d (ppm)=7.08–6.95 (CH); 4.52–4.42 (CH$_2$); 3.74–3.67 (CH); 3.60–3.41 (CH$_2$); 3.13–2.96 (CH); 2.69–2.51 (CH$_2$); 2.23–2.09 (CH); 1.08 (t, J=7 Hz, CH$_3$).

$^{13}$CNMR (CDCl$_3$): d (ppm)=205.3 (C=O), 168.4 (C=O), 129.1 (C—H), 95.6 (CH$_2$), 55.2 (C—H), 43.1 (CH$_2$), 35.9 (CH$_2$), 19.3 (CH$_2$), 7.3 (CH$_3$)

HCl (20%, 300 ml) is heated to gentle boiling in a 3-necked flask having a dropping funnel and water separator with reflux condenser. A solution of the crude 3-propionyl-1-vinyl-2-pyrrolidone (40.4 g, 240 mmol) in THF (60 ml) is added dropwise from the dropping funnel (10 min) and the batch mixture is kept at 100° C. (IT). The acetaldehyde/THF mixture (47 ml) collected in the water separator is discarded. The mixture is kept at this temperature for 6 h, cooled and extracted with ether (200 ml). The 2-ethyl-1-pyrroline is deposited from the HCl-acidic water phase by alkalization to pH 9–10 in the cold (5–10° C.). The deposited oil is taken up in diethyl ether (150 ml) and the water phase is extracted with diethyl ether (300 ml). The ether phases are combined, dried (K$_2$CO$_3$) and concentrated in a weak vacuum (240 mmHg, 45° C.). 18.4 g of 2-ethyl-1-pyrroline are obtained as a yellow-colored oil (about 94%).

B.p.=109.5 (760 mmHg); yield: 79%, C$_6$H$_{11}$N, MW=97.16.

IR (NaCl): 1/λ (cm$^{-1}$) 3378, 2969, 2937, 2870, 1644, 1462, 1454, 1431, 1371, 1300, 1144, 1093, 1019, 961;

$^1$HNMR (CDCl$_3$): d (ppm)=3.38–3.76 (m; CH$_2$); 2.52–2.34 (m; 2 CH$_2$); 1.89 (quin.; CH$_2$, J=7.8 Hz); 1.15 (t; CH$_3$, J=7.6 Hz); $^{13}$CNMR (CDCl$_3$): d (ppm)=179.8, 60.5, 36.9, 26.8, 22.4, 10.6.

b) 6-(4-Fluorophenyl)-7-methyl-2,3-dihydro-1H-pyrrolizine

2-Bromo-1-(4-fluorophenyl)-1-ethanone (19.53 g, 90 mmol) is added to the oily ethyl-1-pyrroline (17.55 g, 180 mmol) in portions in a 500 ml flask, the exothermically reacting mixture cooling between the additions. The mixture of the reaction components is heated in an oil bath (100° C.) with stirring (30 min). The course of the reaction is monitored by tlc.

The cooled mixture is treated with CH$_2$Cl$_2$ (250 ml) and deposited salts are washed out in a separating funnel using two portions of HCl (3%, 40 ml). The CH$_2$Cl$_2$ phase is washed with water (50 ml), dried (Na$_2$SO$_4$ sicc.) and concentrated.

As a residue, 14.04 g of 6-(4-fluorophenyl)-7-methyl-2,3-dihydro-1H-pyrrolizine remain as a brown viscous oil (about 90%).

Yield: 72%; C$_{14}$H$_{14}$FN, MW=215.27.

$^1$HNMR (CDCl$_3$): d (ppm)=7.39–7.30 (m, 2H, F-ar.); 7.08–6.98 (m, 2H, F-ar.); 6.67 (s, 1H, 5-H); 3.954 (t; 2H, CH$_2$, J=7 Hz); 2.801 (t; 2H, CH$_2$, J=7 Hz); 2.487 (quin.; CH$_2$, J=7 Hz); 2.125 (s; 3H, CH$_3$);

$^{13}$CNMR (CDCl$_3$): d (ppm)=161.04 (d, C—F, J=242 Hz), 135.58 (d, J=2.0 Hz), 133.51 (d, J=2 Hz), 128.87 (d, J=7.5 Hz); 127.65; 115.025 (d, J=20.9 Hz); 111.11 (pyrrole-C—H); 106.71; 46.47; 27.44; 23.14; 10.86.

c) Ethyl 4-[2-(4-fluorophenyl)-1-methyl-6,7-dihydro-5H-pyrrolizine-3-yl]-4H-pyridine-1-carboxylate The solution of 6-(4-fluorophenyl)-7-methyl-2,3-dihydro-1H-pyrrolizine (1.72 g, 8.0 mmol) in CH$_2$Cl$_2$ (55 ml) is firstly treated at 0° C. (ice bath) with pyridine (1.6 ml, 1.58 g, 20 mmol) and dropwise with the solution of ethyl chloroformate (2.1 g, 19.5 mmol) in CH$_2$Cl$_2$ (25 ml) (10 min). After a temperature rise to 3–6° C., the cooling agent is removed and the mixture is stirred for 1 h at RT, then heated to boiling temperature (36° C.) for 15 min. Then and after refluxing for a further hour, in each case 2 further portions of pyridine (each 0.8 ml, 10 mmol) and chloroformic acid (each 1.05 g, 10 mmol) are added dropwise and after a total of 3 h the reaction is terminated. The dark-colored batch solution is poured onto ice water (100 ml), stirred for 15 min and then the phases are separated. The water phase is extracted with CH$_2$Cl$_2$ (100 ml) and the combined organic phase is washed with water (50 ml), dried (Na$_2$SO$_4$ sicc.) and concentrated. As a residue, 2.69 g of dark oil (91.9% crude) remain which still contains residues of unreacted 6-(4-fluorophenyl)-7-methyl-2,3-dihydro-1H-pyrrolizine and was employed without further purification in the next stage.

Yield: 91%; C$_{22}$H$_{23}$FN$_2$O$_2$; MW=366.44.

d) 6-(4-Fluorophenyl)-7-methyl-5-(4-pyridyl)-2,3-dihydro-1H-pyrrolizine

Potassium tert-butoxide (3.36 g, 30 mmol) is added to the solution of the dihydropyridine compound from example 21,c (1.83 g, 5 mmol) in tert-butanol (30 ml) obtained at RT, and the mixture is firstly intensively stirred with admittance of air for 1 h at RT, then under reflux for 1 h. The solution is concentrated, and the residue is taken up with water (40 ml) and extracted with ethyl acetate (100 ml). The ethyl acetate phase is washed with water (20 ml), dried (Na$_2$SO$_4$ sicc.) and concentrated. The attempt to crystallize this residue (1.03 g) from ether (3 ml) was not successful.

The purification of the substance was carried out by cc ($Al_2O_3$, ether):

The residue obtained from fractions 33–42 crystallizes from ether: 0.14 g.

Yield: 10%; $C_{19}H_{17}FN_2$; MW=292.36

$^1$H-NMR ($CDCl_3$) δ[ppm]=8.40–8.37/7.00–6.97 (AA'BB'; 4H, -pyridyl); 7.20–7.11 (m; 2H, ar.); 7.06–6.96 (m; 2H, ar.); 4.10 (t; J=7.0 Hz, $CH_2$); 2.885 (t; J=9.4 Hz, $CH_2$); 2.54 (quin; J=7.1 Hz, $CH_2$), 1.99 (s; $CH_3$).

EXAMPLE 22

6-(4-Fluorophenyl)-5-(4-pyridyl)-2,3-dihydro-1H-pyrrolizine a) 1-Fluoro-4-(2-nitrovinyl)benzene The mixture of 4-fluorobenzaldehyde (12.4 g, 0.1 mol), anhydrous ammonium acetate (7.8 g, 0.101 mol) and nitromethane (8.1 ml, 9.15 g, 0.15 mol) in glacial acetic acid (68 ml) are heated to reflux (110° C.) for 3.5 h. The cooled mixture is treated with ice water (80 ml), whereupon brown needles crystallize out. After placing in the cold in an ice bath for 30 min, the crystals are filtered off with suction, washed with water (60 ml) and dried for 16 h in vacuo (desiccator) over $P_2O_5$: 13.2 g (81.8%).

The crystals are recrystallized from acetic acid (50%, 130 ml) in the presence of heat: the slightly pale green crystals crystallizing in the cold (2 fractions) are washed with water (60 ml) and dried as above: 9.76 g, and 1.09 g.

Yield: 67% (10.8 g), $C_8H_6FNO_2$; MW=167.14

IR (KBr): 1/λ ($cm^{-1}$)=3111, 1637, 1595, 1501, 1341, 1230, 1164, 965, 827, 515;

$^1$H-NMR ($CDCl_3$): δ[ppm]=8.02–7.96 (d, 1H, J=13.7 Hz, —$C_bH$=$CH_aNO_2$); 7.60–7.50 (m, 3H, ar.+—$C_bH$=$H_aNO_2$); 7.20–7.11 (t, 2H, J=8.5 Hz, ar.).

b) 6-(4-Fluorophenyl)-5-(4-pyridyl)-2,3-dihydro-1H-pyrrolizine 1-(Pyridine-4-carbonyl)pyrrolidine-2-carboxylic acid (example 19A, b; 60%, 2.0 g, 5.5 mmol) dissolved at 80° C. in acetic anhydride (16 ml) is treated with 1-fluoro-4-(2-nitrovinyl)-benzene (1.32 g, 7.9 mmol) and heated to 130° C. (IT). At 110° C. begins the release of $NO_2$ and $CO_2$, which is complete after 60 min. After a total of 2 h at 110–130° C., the batch is allowed to cool and to stand at RT for 16 h.

The mixture is partitioned between water (70 ml) and ethyl acetate (50 ml), the organic phase is separated off, the $H_2O$ phase is extracted with ethyl acetate (100 ml) and the combined ethyl acetate phase is dried ($Na_2SO_4$ sicc.) and concentrated.

The isolation of the product was carried out by means of CC ($Al_2O_3$, ether): fractions 17–60, (rf=0.5): residue crystallizes from diisopropyl ether, 0.32 g (needles, 2nd crystallization fraction from the mother liquor 0.1 g).

Yield: 16.6% (0.32 g), $C_{18}H_{15}FN_2$; MW=278.33

IR (KBr): 1/λ ($cm^{-1}$)=3111, 1637, 1595, 1501, 1341, 1230, 1164, 965, 827, 515;

$^1$H-NMR ($CDCl_3$) δ[ppm]=8.49–8.45/7.13–7.10 (AA'BB'; 4H, -pyridyl); 7.25–7.17 (m; 2H, ar.); 6.99–6.90 (m; 2H, ar.); 6.03 (s; H, pyrrolizine-C5-H); 4.06 (t; J=7.0 Hz, $CH_2$); 2.95 (t; J=7.3 Hz, $CH_2$); 2.54 (quin; J=7.2 Hz, $CH_2$);

$^{13}$C-NMR ($CDCl_3$): δ[ppm]=164.0, 159.2, 150.0 140.6, 139.6, 132.8, 132.7, 130.1, 130.0, 128.3, 122.8, 115.6, 115.2, 120.1, 46.9, 27.5, 24.5.

EXAMPLE 23

7-(4-Fluorophenyl)-3,3-dimethyl-8-pyridin-4-yl-3,4-dihydro-2H-pyrrolo[2,1-b][1,3]thiazine a) 4-(4-Fluorophenyl)-3-pyridin-4-yl-5H-furan-2-one A solution of K tert-butoxide (33.7 g, 0.3 mmol) in MeOH (220 ml), which is prepared with ice cooling, is added dropwise to a suspension of 4-pyridylacetic acid hydrochloride (25.9 g, 0.15 mol) in anhydrous MeOH (150 ml). After stirring at RT for 1 h, the methanol is distilled off in vacuo and the residue of the potassium salts is taken up in DMF abs. (250 ml). 2-Bromo-1-(4-fluorophenyl)ethanone (23.9 g, 0.11 mol) is stirred in in portions (5 g) and stirring of the mixture is continued at RT for 2 h. After this, it is poured onto water (1.5 l) and extracted by stirring with $CHCl_3$ (250 ml) for 30 min and the $CHCl_3$ phase is separated off in a separating funnel. The water phase separated off is extracted with $CHCl_3$ (300 ml), and the combined $CHCl_3$ extracts are washed with water (200 ml), dried over $Na_2SO_4$ sicc. and concentrated. The dark-green semicrystalline residue is digested with EtOH (50 ml), and the crystals are filtered off with suction, washed with EtOH (20 ml) and dried: 18.8 g of yellow-green crystals.

M.p. 157.0° C.; yield: 50%, $C_{15}H_{10}FNO_2$; MW=255.25;

IR (KBr): 1/λ ($cm^{-1}$)=1746, 1647, 1602, 1509, 1233, 1161, 1037, 827, 839;

$^1$H-NMR ($CDCl_3$): δ[ppm]=8.68–8.64 (m, 2H, AA' pyridyl.); 7.38–7.26 (m, 4H, BB' pyridyl. +F-ar.); 7.14–7.05 (m, 2H, F-ar.); 5.19 (s, 2H, $CH_2$);

b) 4-(4-Fluorophenyl)-1-(3-hydroxy-2,2-dimethyl-propyl)-3-pyridin-4-yl-1,5-dihydropyrrol-2-one Equimolar amounts of neopentanolamine (3-hydroxy-2,2-dimethyl-propylamine, 36.3 g, 0.35 mol) and glacial acetic acid (21.0 g, 0.35 mol) are homogeneously mixed with evolution of heat and the still warm mixture is heated to 105° C. (IT) by lowering it into a temperature-controlled oil bath. 4-(4-Fluorophenyl)-3-pyridin-4-yl-5H-furan-2-one (17.8 g, 0.07 mol) is stirred into this neopentanolammonium acetate melt in 4 portions (15 min) and the reaction mixture is heated for a further 1.5 h. The cooled reaction mixture is treated with sat. $NaHCO_3$ solution and ethyl acetate (50 ml) and intensively stirred (30 min). The crystals deposited are filtered off with suction, washed with ethyl acetate and dried in vacuo: 12.3 g.

Yield: 52%, $C_{20}H_{21}FN_2O_2$; MW=340.40

IR (KBr): 1/λ ($cm^{-1}$)=3410, 1662, 1598, 1506, 1381, 1228, 1049, 831;

$^1$H-NMR ($CDCl_3$) δ[ppm]=8.63–8.59 (m, 2H, AA' pyridyl.); 7.351–7.225 (m, 4H, BB' pyridyl. +F-ar.); 7.085–6.995 (m, 2H, F-ar.); 4.44 (s, 2H, C-5-$CH_2$); 3.40 (s, 2H, $CH_2OH$); 3.27 (br, 2H, $CH_2N$); 1.88 (br, OH), 1.00 (s, 6H, $CH_3$).

c) 7-(4-Fluorophenyl)-3,3-dimethyl-8-pyridin-4-yl-3,4-dihydro-2H-pyrrolo[2,1-b][1,3]-thiazine 4-(4-Fluorophenyl)-1-(3-hydroxy-2,2-dimethylpropyl)-3-pyridin-4-yl-1,5-dihydropyrrol-2-one (5.1 g, 15 mmol) and phosphorus pentasulfide ($P_2S_5$, 2.5 g, 11.2 mmol) are intimately triturated and the trituration is then heated at 210° C. under argon in an oil bath for 3 h. The solidified glassy mass is dissolved in ethyl acetate (40 ml) and NaOH (10%, 40 ml). The ethyl acetate phase is separated off, washed with water, dried ($Na_2SO_4$ sicc.) and concentrated. The residue (3.8 g) is purified by cc ($SiO_2$/ethyl acetate):

The residue obtained from fraction 2 (rf=0.9) crystallizes from diisopropyl ether: 0.6 g.

Yield: 11.8%, $C_{20}H_{19}FN_2S$; MW=338.45

IR (KBr): 1/λ ($cm^{-1}$)=3432, 1964, 1597, 1535, 1498, 1385, 1212, 1164, 991, 840, 816, 591, 517;

$^1$H-NMR ($CDCl_3$) δ[ppm]=8.465–8.430 (m, 2H, AA' pyridyl.); 7.262–7.05 (m, 4H, BB' pyridyl. +F-ar.); 7.00–6.935 (m, 2H, F-ar.); 6.71 (s, 1H, CH=); 3.70 (s, 2H, $CH_2$); 2.80 (s, 2H, $CH_2$); 1.22 (s, 6H, $C(CH_3)_2$);

GC-MS (EI, 70 eV): m/z (rel Int. [%])=340 (9), 339 (28), 338 (100), 282 (8), 281 (30).

EXAMPLE 24
7-(4-Fluorophenyl)-3,3-dimethyl-8-pyridin-4-yl-3,4-dihydro-2H-pyrrolo[2,1-b][1,3]-oxazine 4-(4-Fluorophenyl)-1-(3-hydroxy-2,2-dimethylpropyl)-3-pyridin-4-yl-1,5-dihydropyrrol-2-one (example 23, b; 2.55 g, 7.5 mmol) dissolved in $CH_2Cl_2$ (30 ml) is treated with pyridine (2.82 g, 35.6 mmol) and then dropwise with methanesulfonyl chloride (3.84 g, 33.8 mmol) and the mixture is stirred at RT for 16 h. Water (20 ml) is added and after stirring for 15 min the phases are separated in a separating funnel. The $CH_2Cl_2$ phase is firstly washed until neutral with sat. $NaHCO_3$ soln (10 ml), dried over $Na_2SO_4$ sicc. and concentrated. The residue obtained (1.9 g, 51%) of the dimethanesulfonate (+monomethane-sulfonate) is taken up in methanolic KOH (25 ml, 2N) and heated to reflux under argon for 16 h. After this, it is diluted with semisaturated sodium chloride solution (150 ml) and extracted with ethyl acetate. The ethyl acetate extracts are dried over $Na_2SO_4$ sicc. and concentrated. The residue (0.8 g) is crystallized from diisopropyl ether, and the crystals are filtered off with suction and dried in vacuo: 0.3 g of crystals.

M.p. 173.0° C., yield: 12.4%, $C_{20}H_{19}FN_2O$; MW=322.39

IR (KBr): $1/\lambda$ $(cm^{-1})$=2962, 2870, 1599, 1549, 1505, 1389, 1217, 1142, 1006, 992, 823, 835, 809, 580;

$^1$H-NMR ($CDCl_3$) $\delta$[ppm]=8.371–8.340 (m, 2H, AA' pyridyl.); 7.262–7.10 (m, 4H, BB' pyridyl. +F-ar.); 7.05–6.90 (m, 2H, F-ar.); 6.19 (s, 1H, CH=); 3.95 (s, 2H, $CH_2$); 3.71 (s, 2H, $CH_2$); 1.185 (s, 6H, $C(CH_3)_2$);

GC-MS (70 eV) m/e=322(100%); 293(>10%), 238.

What is claimed is:

1. A 4-pyridyl- or 2,4-pyrimidinyl-substituted compound of formula I, in which the variables have the following meanings;

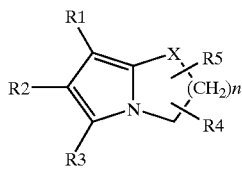

| X | n | $R_1$ | $R_2$ | $R_3$ | $R_4$ | $R_5$ |
|---|---|---|---|---|---|---|
| $CH_2$ | 1 | $CO_2Et$ | 4-pyridyl | 4-F-phenyl | H | H |
| $CH_2$ | 1 | 4-pyridyl | $CO_2Et$ | 4-F-phenyl | H | H |
| $CH_2$ | 1 | $CO_2H$ | 4-pyridyl | 4-F-phenyl | H | H |
| $CH_2$ | 1 | $CH_2OH$ | 4-pyridyl | 4-F-phenyl | H | H |
| $CH_2$ | 1 | $CH_3$ | 4-pyridyl | 4-F-phenyl | H | H |
| $CH_2$ | 1 | H | 4-pyridyl | 4-F-phenyl | H | H |
| $CH_2$ | 1 | $CO_2Et$ | 4-pyridyl | 2-thienyl- | H | H |
| $CH_2$ | 1 | 4-pyridyl | $CO_2Et$ | 2-thienyl- | H | H |
| $CH_2$ | 1 | $CO_2H$ | 4-pyridyl | 2-thienyl- | H | H |
| $CH_2$ | 1 | H | 4-pyridyl | 2-thienyl- | H | H |
| $CH_2$ | 1 | $CO_2Et$ | 4-pyridyl | 5-Cl-2-thienyl- | H | H |

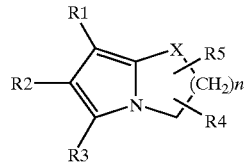

| X | n | $R_1$ | $R_2$ | $R_3$ | $R_4$ | $R_5$ |
|---|---|---|---|---|---|---|
| $CH_2$ | 1 | 4-pyridyl | $CO_2Et$ | 5-Cl-2-thienyl- | H | H |
| S | 1 | $CO_2Et$ | 4-pyridyl | 4-F-phenyl | H | H |
| S | 1 | 4-pyridyl | $CO_2Et$ | 4-F-phenyl | H | H |
| S | 1 | $CO_2H$ | 4-pyridyl | 4-F-phenyl | H | H |
| S | 1 | $CH_2OH$ | 4-pyridyl | 4-F-phenyl | H | H |
| S | 1 | CH3 | 4-pyridyl | 4-F-phenyl | H | H |
| S | 1 | H | 4-pyridyl | 4-F-phenyl | H | H |
| $CH_2$ | 2 | $CO_2Et$ | 4-pyridyl | 4-F-phenyl | H | H |
| $CH_2$ | 2 | 4-pyridyl | $CO_2Et$ | 4-F-phenyl | H | H |
| $CH_2$ | 2 | $CH_2OH$ | 4-pyridyl | 4-F-phenyl | H | H |
| $CH_2$ | 2 | $CH_3$ | 4-pyridyl | 4-F-phenyl | H | H |
| $CH_2$ | 2 | H | 4-pyridyl | 4-F-phenyl | H | H |
| $CH_2$ | 1 | $CO_2Et$ | 4-F-phenyl | 4-pyridyl | H | H |
| $CH_2$ | 1 | 4-F-phenyl | $CO_2Et$ | 4-pyridyl | H | H |
| $CH_2$ | 1 | $CH_2OH$ | 4-F-phenyl | 4-pyridyl | H | H |
| $CH_2$ | 1 | $CH_3$ | 4-F-phenyl | 4-pyridyl | H | H |
| $CH_2$ | 1 | H | 4-F-phenyl | 4-pyridyl | H | H |
| S | 2 | 4-pyridyl | 4-F-phenyl | H | $CH_3$ | $CH_3$ |
| O | 2 | 4-pyridyl | 4-F-phenyl | H | $CH_3$ | $CH_3$ |
| $CH_2$ | 1 | phenyl | 4-F-phenyl | 4-pyridyl | H | H |
| $CH_2$ | 1 | phenyl | 2,4-pyrimidyl | $CH_3$ | H | H |
| $CH_2$ | 1 | 4-F-phenyl | 2,4-pyrimidyl | $CH_3$ | H | H |
| $CH_2$ | 1 | $CH_3$ | 4-F-phenyl | 2,4-pyrimidyl | H | H |
| $CH_2$ | 1 | phenyl | 3-amino-2,4-pyrimidyl | $CH_3$ | H | H |
| $CH_2$ | 1 | 4-F-phenyl | 3-amino-2,4-pyrimidyl | $CH_3$ | H | H |
| $CH_2$ | 1 | $CH_3$ | 4-F-phenyl 3- | amino-2,4-pyrimidyl | H | H | and the optical isomers, physiologically tolerable salts and physiologically easily hydrolyzable esters thereof.

2. A pharmaceutical composition comprising at least one compound as claimed in claim 1, together with a pharmaceutically acceptable additive.

3. A method for the treatment of auto-immune diseases, multiple sclerosis, arthritis, inflammatory bowel disease, septic shock, adult respiratory distress syndrome and transplantations, comprising administering an amount of a compound of the formula I as claimed in claim 1 having immunomodulating action, inhibiting cytokine release, or a combination thereof, to a person who is in need of said treatment.

* * * * *